(12) United States Patent
Scully

(10) Patent No.: US 10,980,510 B2
(45) Date of Patent: Apr. 20, 2021

(54) ULTRASOUND PROBE COUPLERS AND RELATED METHODS

(71) Applicant: Casey K. Scully, Charlotte, NC (US)

(72) Inventor: Casey K. Scully, Charlotte, NC (US)

(73) Assignee: Casey K. Scully, Charlotte, NC (US)

( * ) Notice: Subject to any disclaimer, the term of this patent is extended or adjusted under 35 U.S.C. 154(b) by 0 days.

(21) Appl. No.: 15/648,560

(22) Filed: Jul. 13, 2017

(65) Prior Publication Data

US 2017/0303894 A1 Oct. 26, 2017

Related U.S. Application Data

(63) Continuation-in-part of application No. 14/986,169, filed on Dec. 31, 2015.

(Continued)

(51) Int. Cl.
*A61K 9/00* (2006.01)
*A61B 8/00* (2006.01)
(Continued)

(52) U.S. Cl.
CPC .......... *A61B 8/4281* (2013.01); *A61B 8/4411* (2013.01); *A61B 8/4422* (2013.01);
(Continued)

(58) Field of Classification Search
CPC .................................................. A61B 8/4281
See application file for complete search history.

(56) References Cited

U.S. PATENT DOCUMENTS

| 4,796,632 A | | 1/1989 | Boyd | |
|---|---|---|---|---|
| 5,482,047 A | * | 1/1996 | Nordgren | ................ A61B 8/06 174/263 |

(Continued)

FOREIGN PATENT DOCUMENTS

| WO | WO 2004/062460 A2 | 7/2004 |
|---|---|---|
| WO | WO 2009/009064 A1 | 1/2009 |
| WO | WO 2014/036170 A1 | 3/2014 |

OTHER PUBLICATIONS

çetin, Mustafa Ilker "Effect of Solid Couplants Made of Hydrophilic Polymers in Ultrasonic Testing" *Thesis Submission* The Middle East Technical University, The Graduate School of Natural and Applied Sciences (154 pages) (Dec. 2003).

(Continued)

*Primary Examiner* — Paul W Dickinson
(74) *Attorney, Agent, or Firm* — Myers Bigel, P.A.

(57) ABSTRACT

Couplers for ultrasound probes can have a solid coupler body and a probe attachment member that is secured to a coupler body. The probe attachment member may extend upwardly from the coupler body. The probe attachment member may frictionally and/or adhesively engage with an ultrasound probe, thereby attaching and/or holding the coupler body to an end of the ultrasound probe. The coupler body may include at least one open channel that that extends through the coupler body to define a fluid path. The at least one open channel may be sized to hold and/or contain a fluid and/or gel in and/or on the coupler body and only release the fluid and/or gel when a force is exerted at a top surface of the coupler body. A coupler may be provided in a package in an orientation and easy to use fashion that may aid in attaching the coupler to an end of an ultrasound probe.

26 Claims, 22 Drawing Sheets

Related U.S. Application Data

(60) Provisional application No. 62/361,614, filed on Jul. 13, 2016, provisional application No. 62/101,098, filed on Jan. 8, 2015.

(51) Int. Cl.
*A61K 49/22* (2006.01)
*A61B 8/08* (2006.01)

(52) U.S. Cl.
CPC .......... *A61B 8/4444* (2013.01); *A61K 49/226* (2013.01); *A61B 8/488* (2013.01)

(56) References Cited

U.S. PATENT DOCUMENTS

| | | | |
|---|---|---|---|
| 5,522,878 A | 6/1996 | Montecalvo et al. | |
| 5,650,143 A | 7/1997 | Bergmann et al. | |
| 5,782,767 A | 7/1998 | Pretlow, III | |
| 5,916,546 A | 6/1999 | Sawin et al. | |
| 6,039,694 A * | 3/2000 | Larson | A61B 8/4281 600/459 |
| 6,302,848 B1 * | 10/2001 | Larson | A61L 31/06 600/438 |
| 6,719,699 B2 | 4/2004 | Smith | |
| 7,070,565 B2 | 7/2006 | Vaezy et al. | |
| 2001/0033825 A1 | 10/2001 | Douglas | |
| 2003/0171700 A1 | 9/2003 | Roy et al. | |
| 2003/0233045 A1 | 12/2003 | Vaezy et al. | |
| 2005/0074407 A1 | 4/2005 | Smith | |
| 2005/0215901 A1 | 9/2005 | Anderson et al. | |
| 2006/0184074 A1 | 8/2006 | Vaezy et al. | |
| 2007/0087060 A1 | 4/2007 | Dietrich et al. | |
| 2011/0087107 A1 | 4/2011 | Lindekugel et al. | |
| 2011/0313293 A1 | 12/2011 | Lindekugel et al. | |
| 2012/0277640 A1 | 11/2012 | Lewis et al. | |
| 2014/0180116 A1 | 6/2014 | Lindekugel et al. | |
| 2016/0199027 A1 | 7/2016 | Scully | |

OTHER PUBLICATIONS

Site-Rite Prevue® Ultrasound System, Pinpoint® Disposables *Product Description* http://www.bardaccess.com/products/imaging/siterite-prevue (3 pages) date unknown but believed to be before the priority date of the present application; printed from the internet Dec. 30, 2015.

* cited by examiner

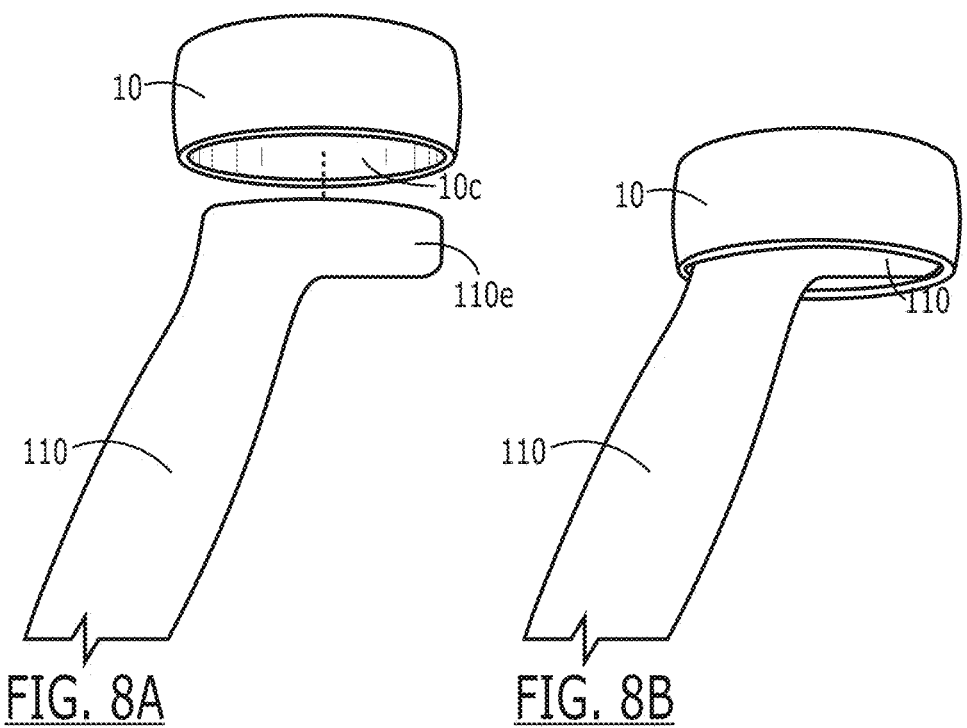
FIG. 8A
FIG. 8B
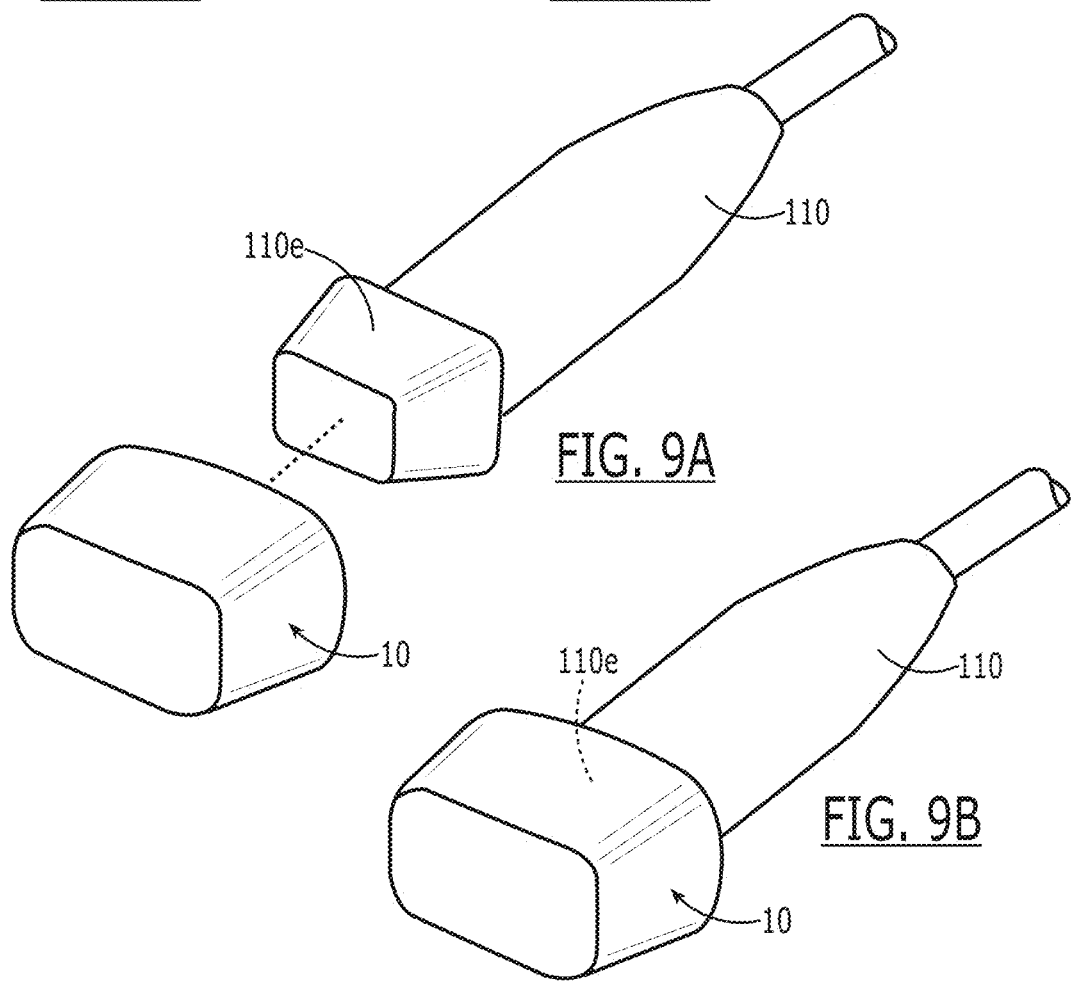
FIG. 9A
FIG. 9B

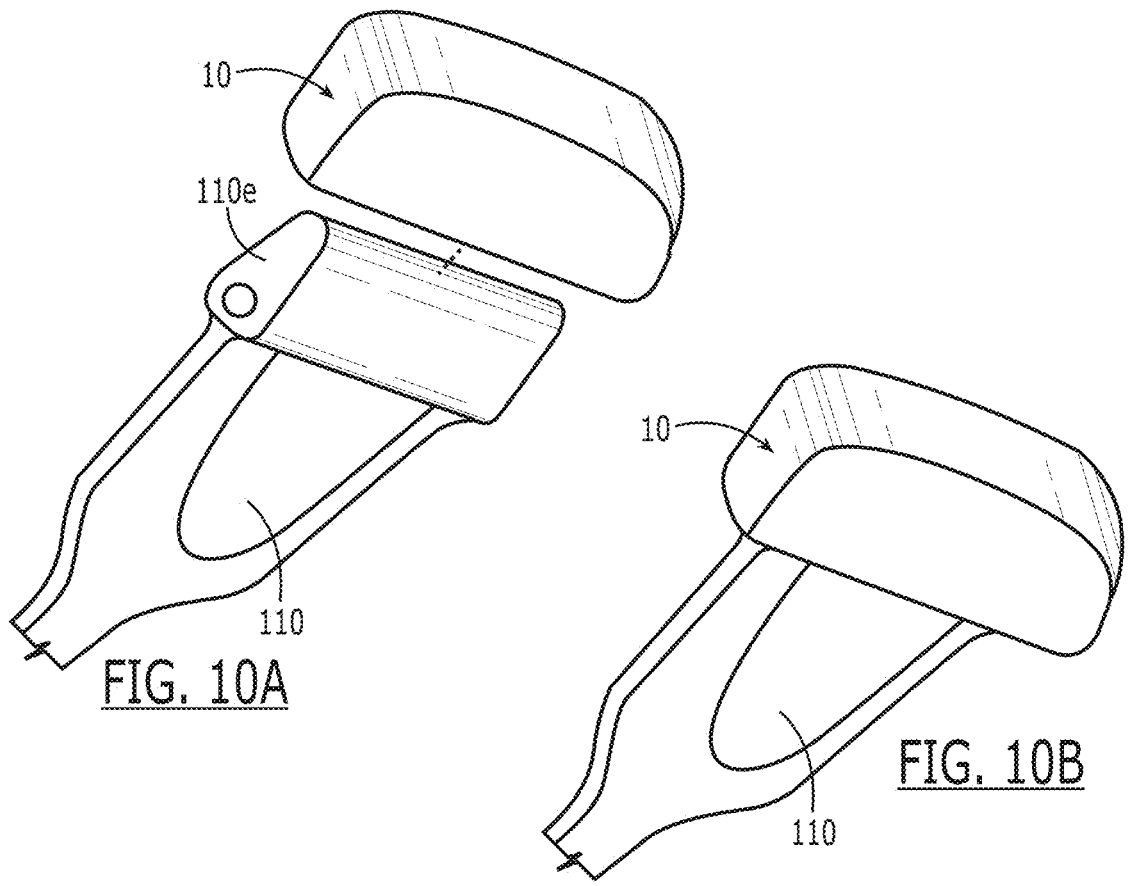
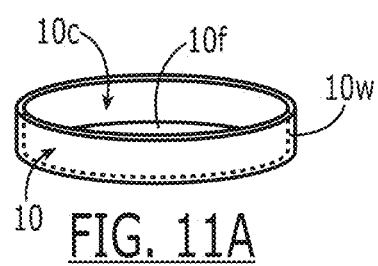
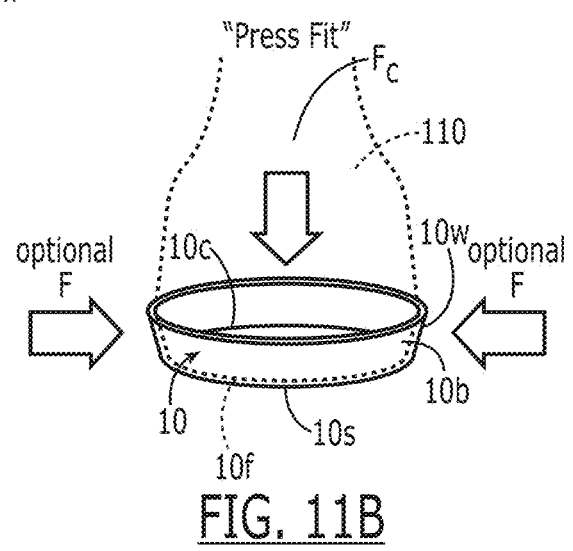

Gel

New device

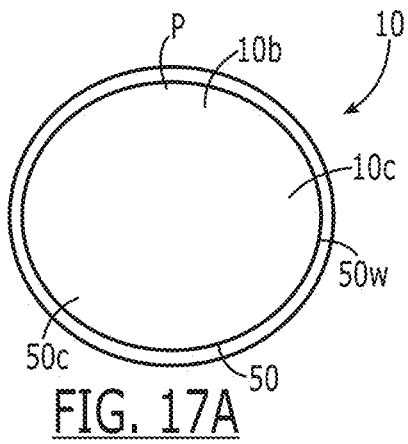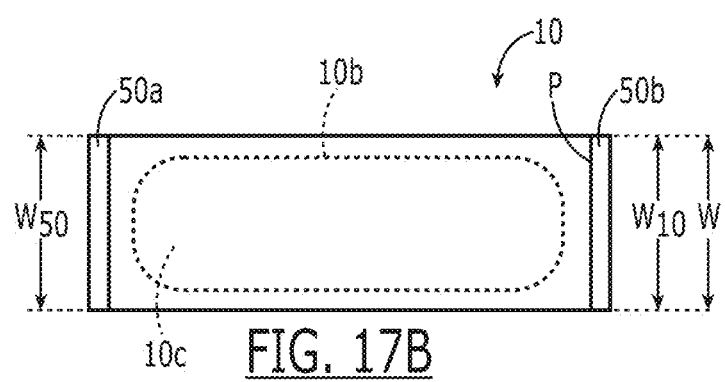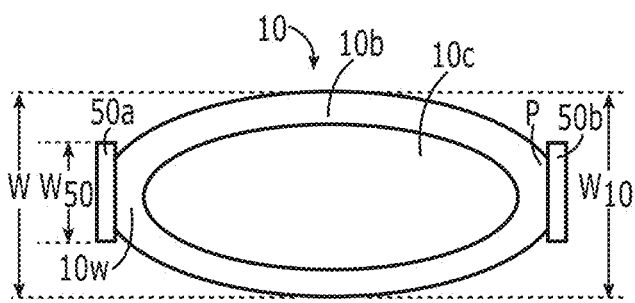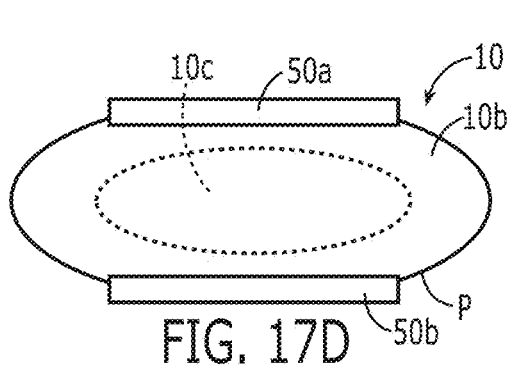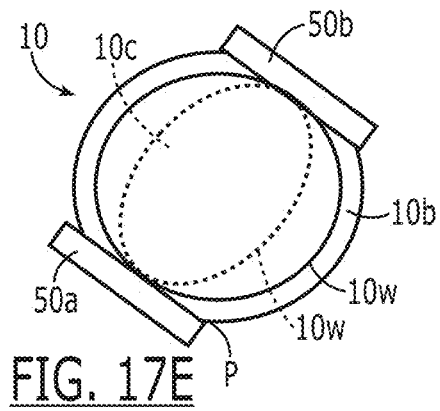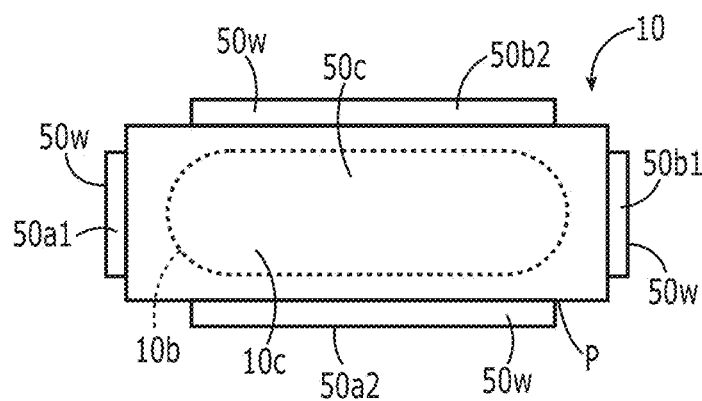

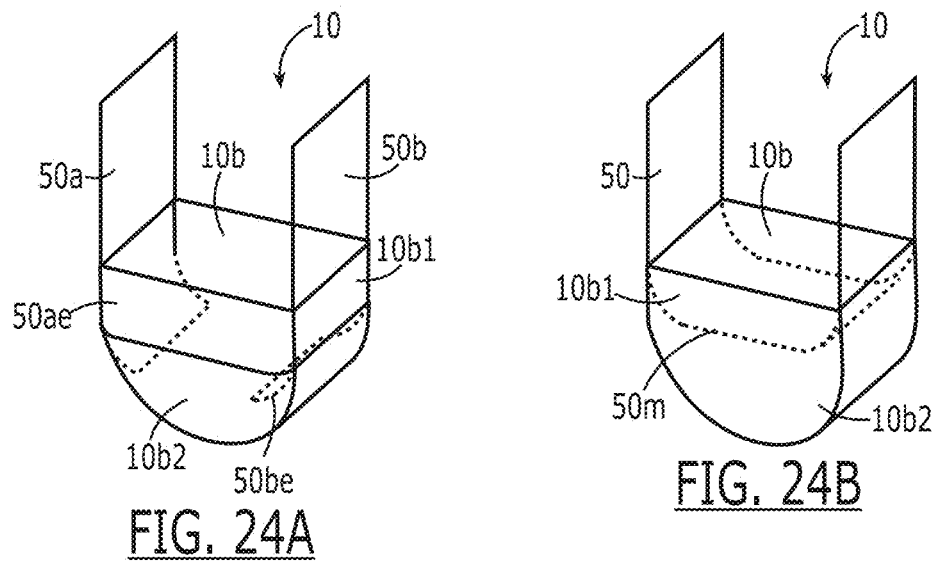
FIG. 24A
FIG. 24B
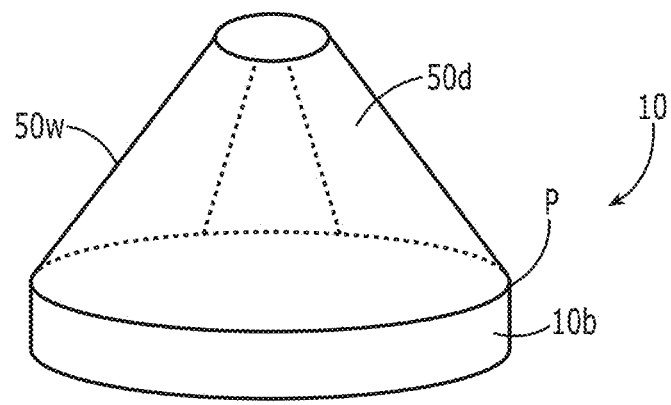
FIG. 25A
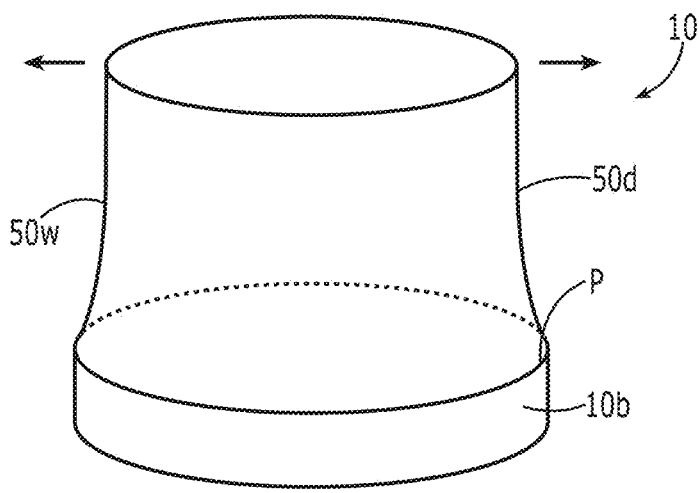
FIG. 25B

ULTRASOUND PROBE COUPLERS AND RELATED METHODS

RELATED APPLICATIONS

This application claims the benefit of and priority to U.S. Provisional Application Ser. No. 62/361,614, filed Jul. 13, 2016, the contents of which are hereby incorporated by reference as if recited in full herein. This application is also a continuation-in-part of U.S. patent application Ser. No. 14/986,169 filed Dec. 31, 2015, which claims the benefit of and priority to U.S. Provisional Application Ser. No. 62/101,098, filed Jan. 8, 2015, the contents of which are each hereby incorporated by reference as if recited in full herein.

FIELD OF THE INVENTION

The present invention relates to ultrasound probe couplers, ultrasound imaging systems, and related methods.

BACKGROUND

Ultrasound imaging can visualize and assess subsurface tissues while posing extremely low risk to the patient and practitioner. As is well known, ultrasound systems produce ultrasound waves transmitted by the ultrasound probe to a subject. Ultrasound waves reflect off objects, tissue or other structure and are detected/received and used to create ultrasound images. An ultrasound "gel" is often applied onto skin by a clinician to facilitate or improve the transmission or reception of sound waves. The ultrasound gel can be provided in bulk or in individual pouches. However, when provide in bulk, the gel may not be maintained or portioned out for use on a patient in a sterile manner, particularly in emergency situations. Gel may need to be reapplied during a procedure and its thickness may vary, which can impact transmission/image clarity. Gel applied directly onto a patient is also messy and can be associated with a risk of infection if not kept sterile prior to use. The gel is also often cold, causing a patient some discomfort or sensitivity, slippery and relatively messy. Also, the ultrasound probe is subject to repeated cleanings that may harm or reduce the life span of a transducer. A recent investigation of current infection control practices for ultrasound coupling gel found medical professionals non-compliant, resulting in a contamination rate of 2.5% either from contamination of ultrasound gel manufacturers or human error. See, e.g., Reg Anesth Pain Med. 2013, September-October; 38(5): 415-24.

Gel pads are also available but are relatively costly. It is believed that gel pads are not favored for clinical use due to one or more of their cost, the fact that a clinician must pick-up and move a gel pad (it does not move with the ultrasound probe, e.g., they are placement dependent) and their use adds an extra step in prepping a patient/probe for ultrasound imaging.

There remains a need for alternative ultrasound probe couplers that are easy to use and can facilitate compliance and/or reduce infection rates.

SUMMARY OF EMBODIMENTS OF THE INVENTION

Embodiments of the invention are directed to ultrasound couplers that include an ultrasound coupler body having a self-supporting, three-dimensional shape; and a probe attachment member that is secured to the coupler body and that in use has a length sufficient to extend upwardly above the coupler body. The ultrasound coupler body can include a first material and the probe attachment member can include a second material with the first material and the second material being different.

The ultrasound coupler body can optionally include a polyhydric alcohol, a thickening agent, and a surfactant.

Other embodiments of the invention are directed to ultrasound couplers that include a semi-rigid, malleable ultrasound coupler body having a self-supporting, three-dimensional shape with a sidewall extending about an open cavity over a floor, wherein the coupler body includes at least one open fluid channel that extends through the coupler body to define a fluid path.

Further embodiments of the invention are directed to ultrasound couplers that include a semi-rigid ultrasound coupler body having a self-supporting, three-dimensional shape.

The coupler body can be solid.

The floor can have a thickness that is less than a thickness of the sidewall.

The coupler body can be configured to be press-fit to a target ultrasound probe so that the end of the ultrasound probe resides in the cavity and the coupler self-attaches thereto.

The coupler body can be formed of a material that self-lubricates and dries as it is applied to skin of a subject to thereby facilitate sliding of the coupler and the probe as a unitary assembly.

The coupler body can have a bottom surface that comprises a material corresponding to a solid deodorant.

The floor can have a thickness between 0.1 mm and 12 mm.

The sidewall can have a (maximal) thickness that is between about 1 mm and about 12 mm.

The sidewall can extend above the floor a distance between about 5 mm and about 25 mm.

The sidewall can extend straight above the floor or tapers outward therefrom.

The sidewall can have a top surface that defines a top of the coupler.

The sidewall can have a thickness between about 1 mm and about 12 mm.

The sidewall can define a flat top surface of the coupler with a corresponding width and/or thickness.

The coupler body can be a monolithic unitary member.

The coupler body can include propylene glycol, dipropylene glycol, sodium stearate, and polypropylene glycol ether of myristyl alcohol.

The coupler body can have a bottom surface that is tacky or sticky to touch.

The coupler body can be held in a container prior to use (typically in a sterile condition).

The coupler body can include one or more of: a polyhydric alcohol, a thickening agent, and a surfactant.

The coupler can be used with an ultrasound probe. The ultrasound probe can have an end that is held in the cavity of the coupler.

An ultrasound gel can be present in and/or added to the cavity of the coupler.

Other embodiments are directed to methods of evaluating a subject by: (a) manually pressing a coupler of the present invention against an outer end portion of an ultrasound probe with the coupler providing a skin to ultrasound probe interface; (b) sliding the probe and the coupler together as a unitary member over skin of subject to obtain ultrasound images; and (c) detaching the coupler from the probe after an ultrasound imaging session.

Still further embodiments are directed to a package including an ultrasound coupler of the present invention.

It is noted that aspects of the invention described with respect to one embodiment, may be incorporated in a different embodiment although not specifically described relative thereto. That is, all embodiments and/or features of any embodiment can be combined in any way and/or combination. Applicant reserves the right to change any originally filed claim or file any new claim accordingly, including the right to be able to amend any originally filed claim to depend from and/or incorporate any feature of any other claim although not originally claimed in that manner. These and other objects and/or aspects of the present invention are explained in detail in the specification set forth below.

Other systems and/or methods according to embodiments of the invention will be or become apparent to one with skill in the art upon review of the following drawings and detailed description. It is intended that all such additional systems, methods, and/or devices be included within this description, be within the scope of the present invention, and be protected by the accompanying claims.

BRIEF DESCRIPTION OF THE DRAWINGS

Other features of the present invention will be more readily understood from the following detailed description of exemplary embodiments thereof when read in conjunction with the accompanying drawings.

FIG. 8A is a schematic illustration of a pre-attached view of a coupler adjacent a target ultrasound probe according to embodiments of the present invention.

FIG. 8B is a schematic illustration of the assembled view of the coupler and probe shown in FIG. 8A.

FIG. 9A is a schematic illustration of a pre-attached view of a coupler adjacent a target ultrasound probe according to embodiments of the present invention.

FIG. 9B is a schematic illustration of the assembled view of the coupler and probe shown in FIG. 9A.

FIG. 10A is a schematic illustration of a pre-attached view of a coupler adjacent a target ultrasound probe according to embodiments of the present invention.

FIG. 10B is a schematic illustration of the assembled view of the coupler and probe shown in FIG. 10A.

FIG. 11A is a schematic illustration of an exemplary coupler according to embodiments of the present invention.

FIG. 11B is a schematic illustration of the coupler shown in FIG. 11A with exemplary press-force vectors that can be used to detachably couple (releasably attach) the coupler to the end of the probe according to embodiments of the present invention.

FIGS. 17A-17F are schematic illustrations of a top view of an ultrasound coupler having a probe attachment member that extends upwardly from the coupler body according to example embodiments of the present invention.

FIGS. 24A and 24B are side perspective views of ultrasound couplers with still other example probe attachment members according to embodiments of the present invention.

FIGS. 25A and 25B are side views of ultrasound couplers with further example probe attachment members according to embodiments of the present invention.

DETAILED DESCRIPTION OF EMBODIMENTS OF THE INVENTION

Figure 1:
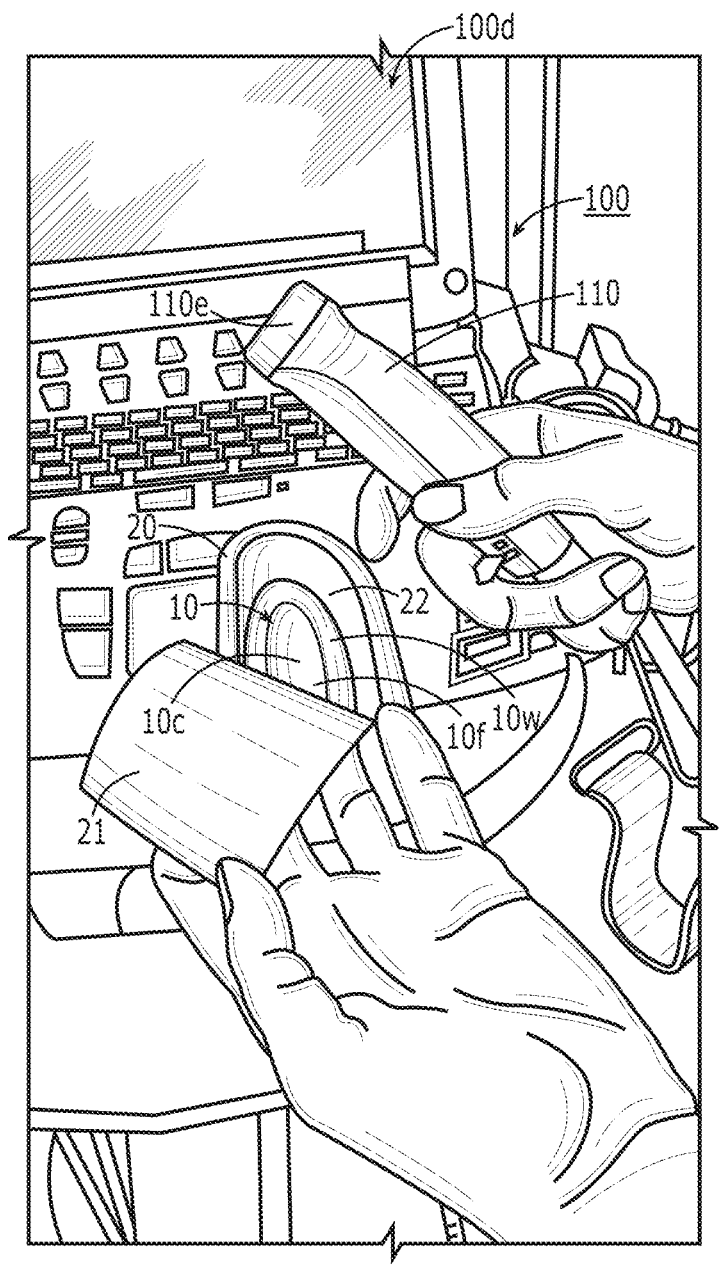
FIG. 1 is a front perspective view of an exemplary malleable ultrasound coupler for an ultrasound probe according to embodiments of the present invention.

The present invention now is described more fully hereinafter with reference to the accompanying drawings, in which embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

Like numbers refer to like elements throughout. In the figures, the thickness of certain lines, layers, components, elements or features may be exaggerated for clarity. The term "Figure" is used interchangeably with the abbreviated versions "FIG." and "Fig." in the specification and figures. Broken lines illustrate optional features, actions or operations unless specified otherwise. One or more features shown and discussed with respect to one embodiment may be included in another embodiment even if not explicitly described or shown with another embodiment.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof as used herein, the term "and/or" includes any and all combinations of one or more of the associated listed items. As used herein, phrases such as "between X and Y" and "between about X and Y" should be interpreted to include X and Y. As used herein, phrases such as "between about X and Y" mean "between about X and about Y." As used herein, phrases such as "from about X to Y" mean "from about X to about Y."

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

It will be understood that when an element is referred to as being "on", "attached" to, "connected" to, "coupled" with, "contacting", etc., another element, it can be directly on, attached to, connected to, coupled with or contacting the other element or intervening elements may also be present. In contrast, when an element is referred to as being, for example, "directly on", "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

It will be understood that, although the terms first, second, etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the present invention. The sequence of operations (or steps) is not limited to the order presented in the claims or figures unless specifically indicated otherwise.

The term "about" means that the recited number or value can vary by +/−20%.

Embodiments of the invention are particularly suitable for human uses and/or veterinary uses.

The term "ultrasound systems" is well known and includes any commercially available system including, but not limited to: Acuson's Sequoia® and Aspen™ platforms; Philips/ATL's HDI® platforms; General Electric's LOGIQ™ platforms; Toshiba's PowerVision™ platforms; Hewlett-Packard's Sonos™ platforms; Siemen's Sonoline® and Elegra™ platforms and the like, as well as portable Doppler systems for various uses such as for limb or muscular evaluation, fetal monitoring, cardiovascular or intracranial uses, for example. The instant invention does not depend on the specific type of ultrasound platform or system used. The term "ultrasound probe" refers to the part of the ultrasound system with the transducer/transducer array that contacts a patient to obtain ultrasound imaging data. The ultrasound probe may have different shapes for different uses and/or systems.

Turning now to the figures, FIGS. 1, 2A-2E, 3A and 3B illustrate an ultrasound system 100 with an ultrasound probe 110 and a semi-rigid ultrasound coupler 10. The ultrasound system 100 can include a display 100d that can show the obtained ultrasound images. The term "semi-rigid" means that the coupler 10 has a self-supported, pre-formed three-dimensional (typically solid) body shape with sufficient rigidity to retain the pre-formed, three-dimensional body shape when apart from the probe 110 (e.g., in a package prior to use, such as in a sterile pouch, bag or other container). In some embodiments, the coupler 10 has a cavity 10c with a floor 10f and/or sidewall 10w. The floor 10f and/or sidewall 10w may be sufficiently malleable or pliable to be able to change in shape when a sufficient (typically manual) compressive force is applied, e.g., a compressive force applied against the sidewall 10w and/or the floor 10f of the coupler 10. The word "malleable" means that at least a portion of the coupler 10 is able to change in shape so as to be able to be pressed permanently out the original pre-formed shape without breaking and/or cracking. Stated differently, the coupler 10 can be formed of a material that can deform under pressure (compressive stress) to a different three-dimensional shape and retain that shape, even after the compressive force is removed.

The coupler body 10b may include a pre-formed cavity 10c. In some embodiments, the coupler body 10b does not include a cavity or the cavity 10c is formed in the coupler body 10b upon and/or after attachment to a probe 110. The coupler body 10b may be malleable such that when the end of a probe 110 is pressed against the coupler body 10b a cavity 10c is formed.

The coupler 10, for respective ultrasound probes 110 of various shapes (e.g., FIGS. 1, 7A, 8A, 9A, and 10A) can have a solid coupler body 10b with a cavity 10c having a semi-rigid, and malleable shape so as to be able to be conform to and/or self-attach to the end of the probe 110e by a user pressing the coupler against the end of the ultrasound probe 110e so that the coupler cavity, e.g., at least the floor 10f thereof and more typically the upwardly extending sidewall as well, takes on the underlying shape of the end of the ultrasound probe 110e while the exterior of the coupler can substantially, if not totally, retain its pre-attached shape. The coupler 10 can have an upwardly extending sidewall 10w forming a perimeter of a cavity 10c which can reside over a closed bottom surface 10f.

The coupler body 10b can have an external pre-formed three-dimensional shape that is the same as or different before and after assembly to the probe 110. The coupler 10 can be solid and have a 3-D shape, and is not inflatable. The coupler body 10b can have any suitable shape and/or size. For example, as shown in FIGS. 17A-17F, the coupler body 10b may have an outer wall that is circular, elliptical, rectangular, and/or the like, but is not limited thereto. Similarly, the probe cavity 10c can have different shapes and/or sizes and may be malleable. In some embodiments, the coupler body 10b may include segments with different shapes and/or sizes. In some embodiments, a lower portion of the coupler body 10b may be elliptical or circular and an upper portion of the coupler body 10b may be rectangular or square or vice versa. Alternatively or in addition, an outer portion of the coupler body 10b may be elliptical or circular and an inner portion of the coupler body 10b surrounding the cavity 10c may be square or rectangular or vice versa.

Referring to FIGS. 17A-17F, 18, 19, 20A-20E, 21A-21D, 22A-22D, 24A, and 24B, in some embodiments, the coupler 10 may include a probe attachment member 50 that may be secured or attached to any portion of the coupler body 10b in any suitable manner. The probe attachment member 50 can be used to attach the coupler 10 to a target ultrasound probe 110 and may stabilize the coupler 10 and/or hold the coupler 10 in a position when attached to the probe 110. The probe attachment member 50 may prevent the coupler 10 from detaching from the probe 110 during use with the probe 110. The probe attachment member 50 may aid the coupler body 10b in moving or sliding in concert the probe 110.

The probe attachment member 50 alone may attach the coupler 10 to a target ultrasound probe 110 or the probe attachment member 50 may be used in conjunction with other attachment mechanisms to hold the coupler 10 to the probe 110. In some embodiments, the coupler 10 has a coupler body 10b having a semi-rigid, yet malleable shape so as to be able to be conform to and/or self-attach to the end of the probe 110 by a user pressing the coupler 10 against the end of the ultrasound probe 110. The probe attachment member 50 can attach the coupler 10 to the probe 110 as a supplemental attachment feature. In some embodiments, the probe attachment member 50 can be the primary attachment mechanism to hold the coupler 10 to a probe 110 and/or can attach the coupler 10 to a probe 110 more securely than the self-attachment of the coupler body 10b.

Figure 18:
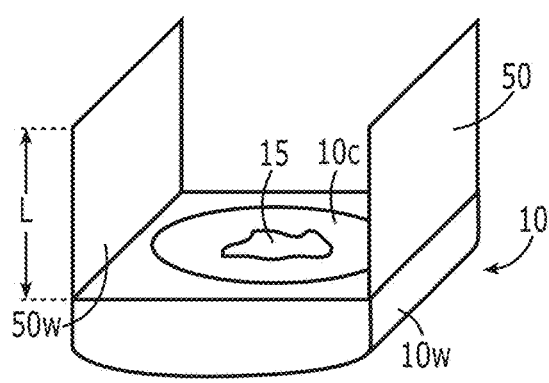
FIG. 18 is a schematic illustration of a side perspective view of an ultrasound coupler having a probe attachment member that extends upwardly from the coupler body according to an example embodiment of the present invention.

In some embodiments, the probe attachment member 50 may be secured or attached to a perimeter portion P of the coupler body 10b and may extend upwardly from the coupler body 10b (FIGS. 17A-17F, 18, 20A-20E, 21A-21D, 22C, and 22D). As shown in FIGS. 17A and 17F, the probe attachment member 50 may define a chamber 50c that at least partially surrounds and/or encloses a top surface of the coupler body 10b. The probe attachment member 50 can have at least one upwardly extending segment that defines a wall 50w of the chamber 50c. The wall 50w may be a solid continuous wall that surrounds the chamber 50c (FIG. 17A) or may be a discontinuous wall (FIG. 17F). The wall 50w may be permeable or impermeable. In some embodiments, a gel 15 may be placed on a top surface of a coupler body 10b (FIG. 19), optionally, the gel 15 may be placed in a cavity 10c of the coupler body 10b (FIG. 18). During operative use, at least some quantity of the gel 15 can reside between the coupler body 10b and the probe 110 when the coupler 10 is in contact and/or attached to the probe 110.

The probe attachment member 50 can include any suitable material. The probe attachment member 50 can include a material that is the same as or different than the material of the coupler 10 and/or coupler body 10b. In some embodiments, the probe attachment member 50 comprises a material that is different than the coupler 10 and/or coupler body 10b.

Figure 19:
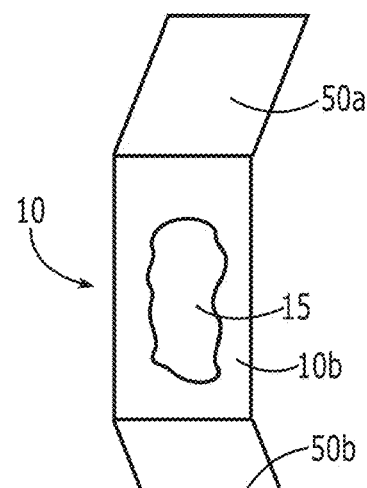
FIG. 19 is a schematic illustration of a top view of an ultrasound coupler having a probe attachment member according to an example embodiment of the present invention.

The probe attachment member 50 may have a structure that is self-supporting or non-self-supporting. In some embodiments, the probe attachment member 50 has a self-supporting structure (i.e., FIGS. 21A-21D) and comprises a material that allows a wall 50w of the probe attachment member 50 to flex out, such as, e.g., when a bottom or lower portion of a probe 110 is positioned in contact with the probe attachment member 50. In some embodiments, the probe attachment member 50 has a non-self-supporting structure (i.e., FIGS. 19 and 22A-22D) and comprises a material that allows at least a portion of a wall 50w of the probe attachment member 50 to conform to an outer surface of a probe 110. When the probe attachment member 50 has a non-self-supporting structure, the probe attachment member 50 can have at least one wall 50w that extends upwardly from the coupler body 10b when in use (e.g., when at least a portion of the wall 50w is attached to a target ultrasound probe 110), but when the wall 50w is not in contact with the probe 110, the wall 50w may drape down or outwardly from the coupler body 10b as shown in FIG. 19. The wall 50w can also be elastic and can be conformable and expand outwardly when in contact with a probe (FIGS. 25A and 25B). As shown in FIG. 25A, the probe attachment member 50d can have a structure that tapers to a smaller configuration at an upper end portion of the probe attachment member 50d distal to the coupler body 10b. The wall 50w of the probe attachment member 50d may be elastic and expand outwardly to provide a larger configuration at the upper end portion of the probe attachment member 50d (FIG. 25B). In some embodiments, the probe attachment member 50d can conform about a probe 110 and can apply a compression force on the probe 110.

Figure 20A:
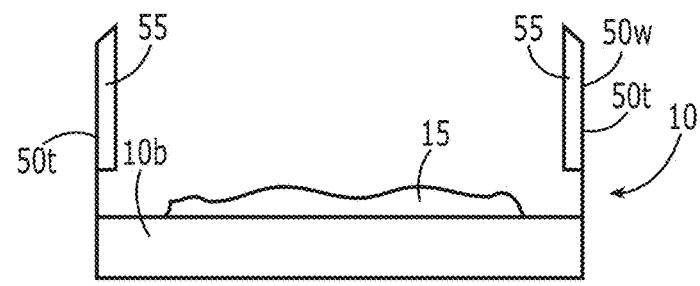
FIG. 20A is a schematic illustration of a side view of an ultrasound coupler having a probe attachment member that comprises an adhesive according to an example embodiment of the present invention.
Figure 20B:
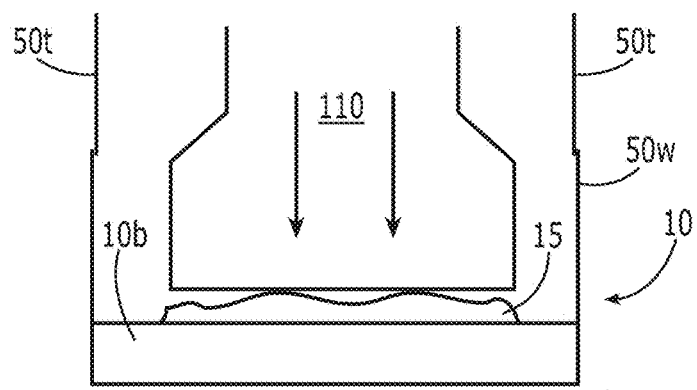
FIG. 20B is a schematic illustration of a side view of the ultrasound coupler shown in FIG. 20A in position with an ultrasound probe according to an example embodiment of the present invention.
Figure 20C:
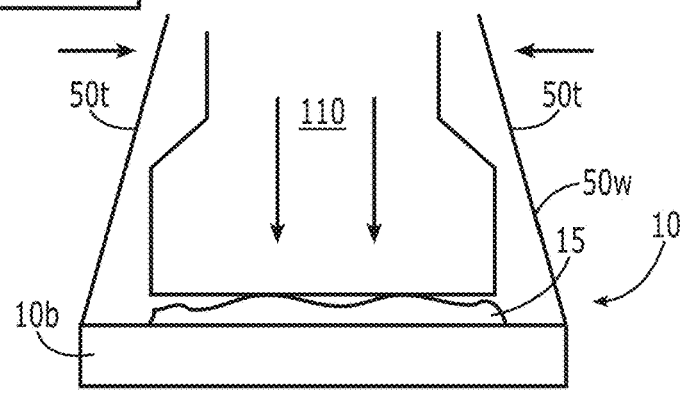
FIG. 20C is a schematic illustration of a side view of the ultrasound coupler shown in FIG. 20B with sides of the probe attachment member further inward toward an ultrasound probe according to an example embodiment of the present invention.
Figure 20D:
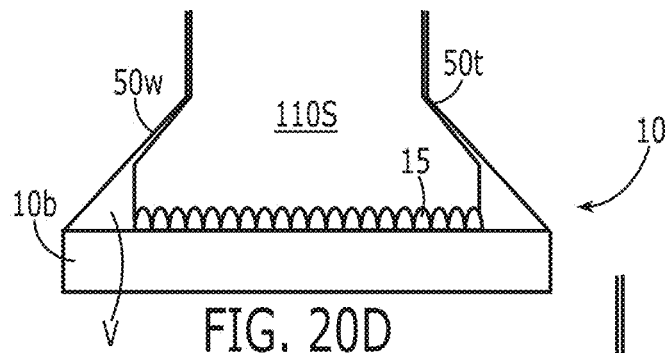
FIG. 20D is a schematic illustration of a side view of the ultrasound coupler shown in FIG. 20C with the probe attachment member attached to the probe according to an example embodiment of the present invention.
Figure 20E:
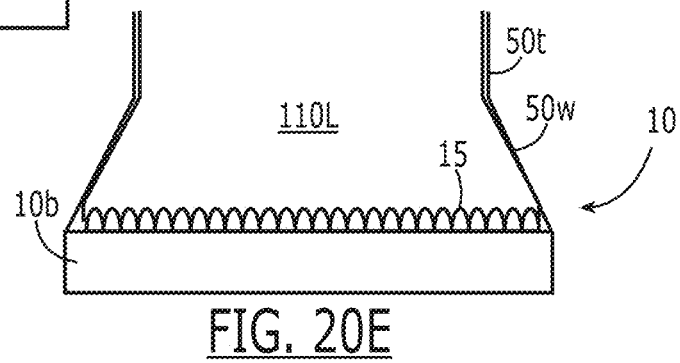
FIG. 20E is a schematic illustration of a side view of the ultrasound coupler shown in FIG. 20A attached to a larger ultrasound probe according to an example embodiment of the present invention.
Figure 21A:
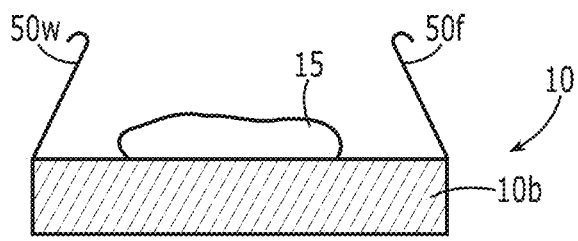
FIG. 21A is a schematic illustration of a side view of an ultrasound coupler including a probe attachment member having a self-supporting structure according to an example embodiment of the present invention.
Figure 21B:
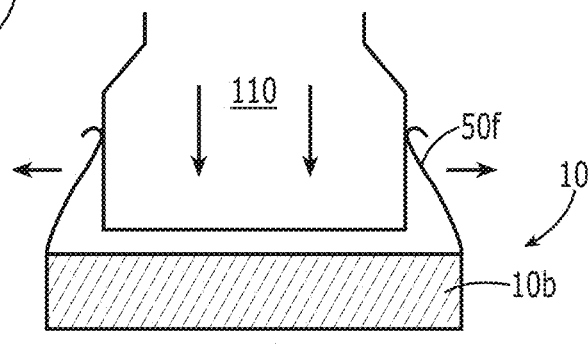
FIG. 21B is a schematic illustration of a side view of the ultrasound coupler shown in FIG. 21A in contact with an ultrasound probe according to an example embodiment of the present invention.
Figure 21C:
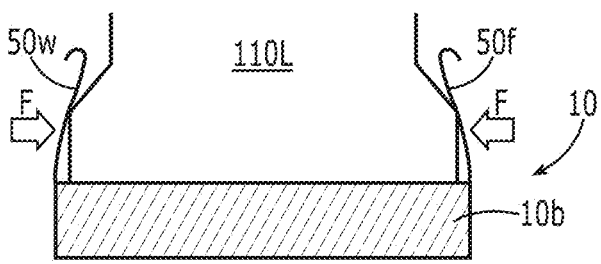
FIG. 21C is a schematic illustration of a side view of the ultrasound coupler shown in FIG. 21A attached to a probe according to an example embodiment of the present invention.
Figure 21D:
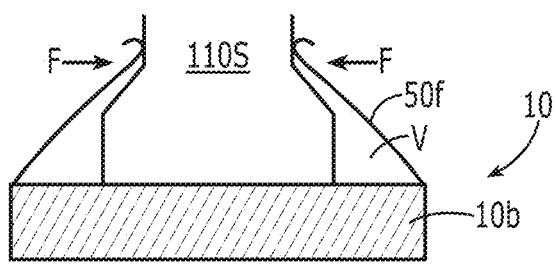
FIG. 21D is a schematic illustration of a side view of the ultrasound coupler shown in FIG. 21A attached to a smaller probe than shown in FIG. 21C according to an example embodiment of the present invention.

The probe attachment member 50 may attach to at least two different sized target probes 110, e.g., a large probe 110L and small probe 110S as shown, for example, in FIGS. 20E and 21C and FIGS. 20E and 21D, respectively. In some embodiments, the probe attachment member 50 may have a wall 50w or portion thereof that conforms to at least a portion of a target ultrasound probe 110.

The probe attachment member 50 may not conform to a probe 110 and/or the coupler body 10b can be larger than the probe 110 such that at least a portion of the wall 50w of the probe attachment member 50 may be spaced apart from the ultrasound probe 110. Thus, a void space V may be present between at least a portion of the probe attachment member 50 and the probe 110 (FIGS. 20E and 21D), typically the void V is proximate to the coupler body 10b.

The probe attachment member 50 can have any suitable size and/or shape. The probe attachment member 50 can be spaced inward from the outer perimeter of the coupler body 10b and can define a chamber 50c that rises a distance above the coupler body 10b.

In use, a wall 50w of the probe attachment member 50 and/or the chamber 50c may rise about 0.5 to about 8 inches above the coupler body 10b, typically about 2 to about 6 inches above the coupler body 10b.

In some embodiments, a probe attachment member 50 and/or wall 50w of the probe attachment member 50 may have a width that is substantially the same as, equal to, greater than, or less than a width of the coupler body 10b, such as, for example, the width of a side of a coupler body 10b from which the probe attachment member 50 is attached. In some embodiments, the coupler body 10b can have a pair of long sides and a pair of short sides. Referring to FIG. 17B, the probe attachment members 50a, 50b may have a width $W_{50}$ that is substantially the same as or equal to the width $W_{10}$ of the coupler body 10b. Alternatively, the probe attachment members 50a, 50b may have a width $W_{50}$ that is less than the width $W_{10}$ of the coupler body 10b (FIG. 17C) or that is greater than the width of the coupler body 10b. A probe attachment member 50 and/or wall 50w of the probe attachment member 50 may have a width that is about 0.5 inches to about 5 inches, typically about 1 inch to about 3 inches.

As shown in FIGS. 17B-17F, the probe attachment member 50 may include two or more probe attachment members 50a, 50b that may be spaced apart and in any orientation relative to each other and/or the coupler body 10b. For example, first and second probe attachment members 50a, 50b may be laterally and/or longitudinally spaced apart and may be positioned at opposing sides of the perimeter P of the coupler body 10b (FIGS. 17B, 17C, 17D, and 17F). In some embodiments, the coupler body 10b may include a sidewall 10w that extends about a cavity 10c and the first and second probe attachment members 50a, 50b may extend upwardly about the sidewalls 10w of the coupler body 10b (FIGS. 17C and 18). First and second probe attachment members 50a, 50b may be circumferentially spaced apart (FIG. 17E). In some embodiments, first, second, third and fourth probe attachment members 50a1, 50b1, 50a2, and 50b2 may be spaced apart about the perimeter P of the coupler body 10b (FIG. 17F).

In some embodiments, the probe attachment member 50 comprises an adhesive 50t on an inner surface thereof as shown in FIGS. 20A-20E. The adhesive 50t may releasably directly or indirectly attach to a surface of a target ultrasound probe 110. The adhesive 50t may be in any suitable form, such as, for example, in the form of a sheet, film, glue, or the like. In some embodiments, the probe attachment member 50 may comprise a fabric including an adhesive 50t or may comprise an adhesive tape. All or at least a portion of the probe attachment member 50 may comprise the adhesive 50t and the adhesive 50t may be covered and/or protected with a releasable liner 55 (FIG. 20A). As shown in FIG. 20B, when the coupler 10 is in contact with a probe 110 the releasable liner 55 may be removed and the adhesive 50t may be moved upwardly and/or inwardly to be placed in contact with an outer surface of the probe 110 (FIG. 20C). In some embodiments, the probe attachment member wall 50w with the adhesive 50t may have a structure that is non-self-supporting or self-supporting, but configured so that the adhesive can attach the wall 50w to a surface of a probe 110. The wall 50w with the adhesive 50t may conformally adhere to at least a portion of a surface of a probe 110, such as a large probe 110L or a small probe 110S (FIGS. 20D and 20E, respectively).

Referring now to FIGS. 21A-21D, the probe attachment member 50 may have a self-supporting structure 50f. The wall 50w can frictionally engage with and/or apply a clamping force F to a target ultrasound probe 110 when in contact with the probe 110. The self-supporting structure 50f may bend or flex outwardly while remaining upright when a probe 110 is placed in contact with the self-supporting structure 50f, such as, e.g., when a probe 110 is forced down to contact the coupler body 10b (FIG. 21B). The self-supporting structure 50f may have sufficient rigidity and mechanical strength to be able to clamp against an outer surface of a probe 110 with a suitable clamping force F as shown by arrows in FIGS. 21C and 21D. The clamping force F may prevent the coupler 10 from detaching from the probe 110 prior to intended and/or when in use with the probe 110 and/or may aid the coupler body 10b in moving or sliding in concert with the probe 110. The wall 50w of the self-supporting structure 50f may be attached at a single lower edge portion and extend upwardly to define a lever arm that can flex outward from the coupler body 10b. In some embodiments, the wall 50w of the self-supporting structure 50f may comprise a spring memory material. In some embodiments, the self-supporting structure 50f may comprise a polymer and may be a plastic.

Figure 22A:
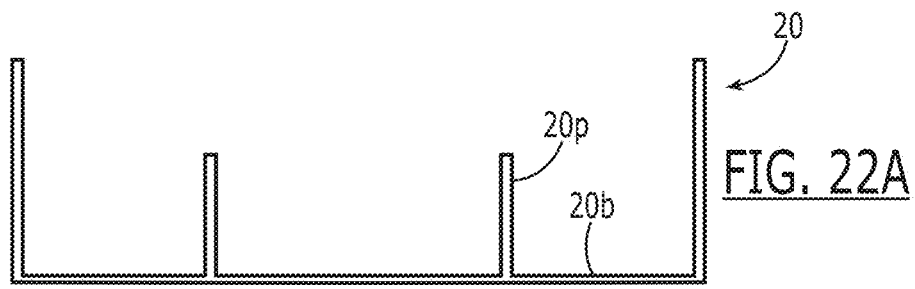
FIG. 22A is a schematic illustration of a side view of a package that can accommodate an ultrasound coupler with a probe attachment member according to example embodiments of the present invention.
Figure 22B:
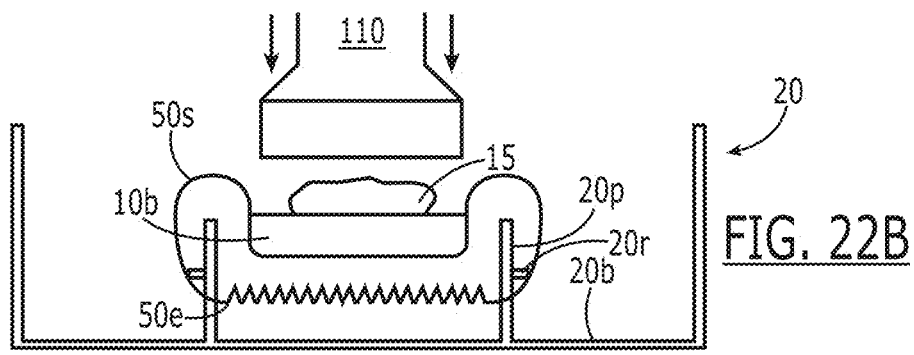
FIG. 22B is a schematic illustration of a side view of the package shown in FIG. 22A with an ultrasound coupler therein and an ultrasound probe aligned therewith according to an example embodiment of the present invention.
Figure 22C:
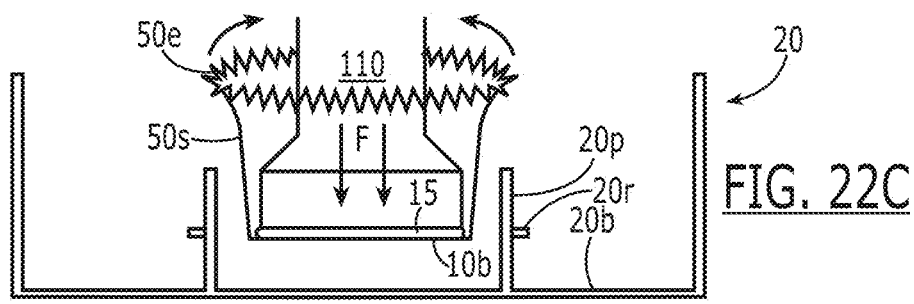
FIG. 22C is a schematic illustration of a side view of the package with the ultrasound coupler shown in FIG. 22B and with an ultrasound probe contacting the coupler and exerting a downward force according to an example embodiment of the present invention.
Figure 22D:
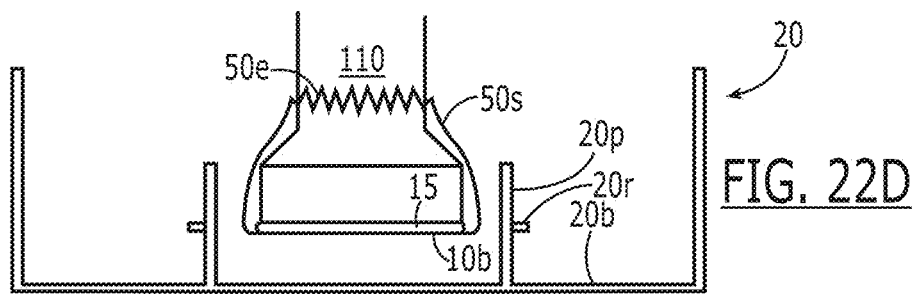
FIG. 22D is a schematic illustration of a side view of the package and the ultrasound coupler shown in FIG. 22C with the ultrasound coupler attached to the ultrasound probe according to an example embodiment of the present invention.

In some embodiments, the attachment member 50 may comprise a flexible sheath 50s as shown in FIGS. 22B-22D. The flexible sheath 50s can include a holding member 50e at any position on the sheath 50s, such as, e.g., at an upper end portion of the sheath 50s (distal to the coupler body 10b) (FIGS. 22B-22D). The holding member 50e may be an integral component of the flexible sheath 50s or may be a separate component. In some embodiments, the holding member 50e is an integral component of the flexible sheath 50s and is positioned at an upper end portion of the sheath 50s. The holding member 50e may be an open or closed band, a clip, a pull rope or string, a velcro (hook and loop) closure, a tie wrap, a strap, and the like. In some embodiments, the sheath 50s may be a polymeric or plastic sheath and the holding member 50e may be a resilient band (e.g., an elastic band such as a rubber band). The holding member 50e can gather a neck or upper end portion of the flexible sheath 50s to a smaller size when in contact with a probe 110 and may hold at least a portion of the sheath 50s against the probe 110.

Figure 23A:
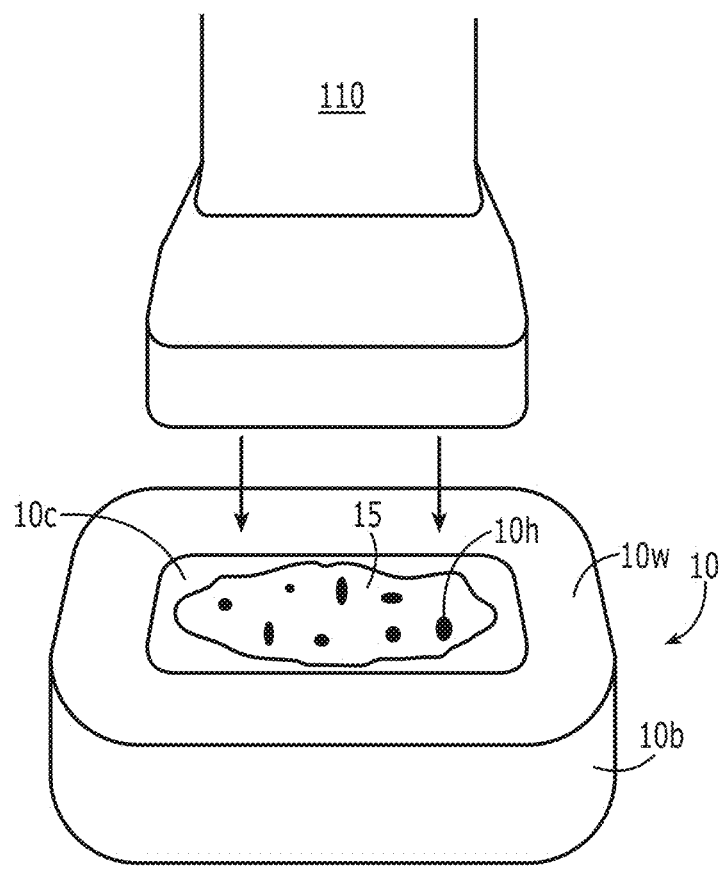
FIG. 23A is a schematic side perspective illustration of an ultrasound coupler containing a plurality of open channels according to example embodiments of the present invention.
Figure 23B:
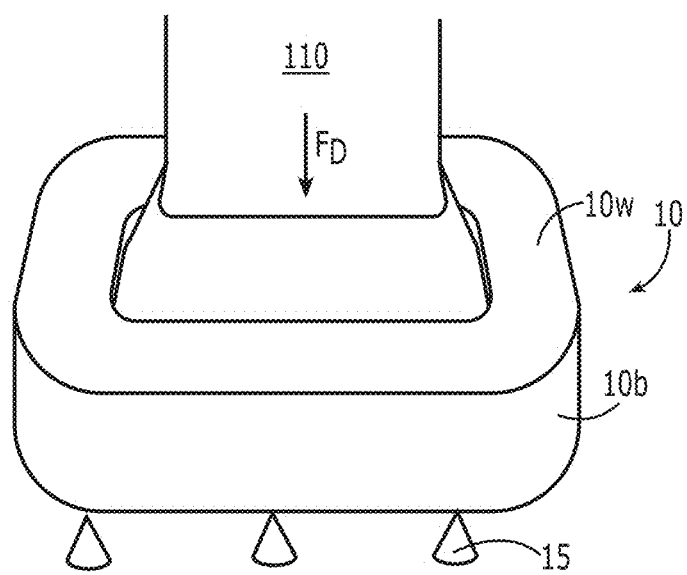
FIG. 23B is a schematic illustration of the ultrasound coupler shown in FIG. 23A attached to the coupler body according to an example embodiment of the present invention.

Referring now to FIGS. 23A and 23B, a coupler body 10b may comprise at least one open channel 10h that extends through the coupler body 10b to thereby define an open fluid path. In some embodiments, a plurality of open channels 10h are provided in the coupler body 10b in any arrangement or number. For example, a plurality of open channels 10h may be arranged in a symmetrical or asymmetrical pattern, may be provided in a particular density or number per square inch, and/or the like. In some embodiments, a plurality of open channels 10h are provided in the coupler body 10b and extend from a top surface of a cavity 10c of the coupler body 10b through the floor 10f of the coupler body 10b. A coupler body 10b may comprise 1 to about 100 open channels 10h per square inch. In some embodiments, the plurality of open channels 10h may be arranged with a greater density in the center or middle of the coupler body 10b and a lower density of open channels 10h toward the outside of the coupler body 10b. In some embodiments, the open channels 10h are regularly spaced apart in aligned columns and/or rows.

An open channel 10h may have a diameter and/or length configured to retain a fluid and/or gel in the coupler body 10b and/or on an upper surface of the coupler body 10b but can release the fluid and/or gel in response to a downward force exerted on the coupler body 10b such as, e.g., upon contact with the probe 110 or when a counter pressure $F_u$, $F_D$ is exerted on the coupler body 10b upon contact with skin of a patient with the probe pressing down against the coupler 10 (FIG. 23B). In some embodiments, an open channel 10h may have a diameter and/or length configured to retain a fluid and/or gel in an upper portion of the open channel 10h. The fluid and/or gel may at least partially extend through the channel 10h prior to use. The diameter of an open channel 10h may be about 0.01 mm to about 2 mm and the length of an open channel 10h may be about 0.1 mm to about 75 mm.

In some embodiments, a gel 15 may be provided on a top surface of the coupler body 10b and/or in a cavity 10c of the coupler body 10b, and less than 10% of the gel 15 may pass through the channel(s) 10h out the bottom of the coupler body 10b prior to a force being exerted on the coupler body 10b and/or cavity 10c. In some embodiments, a coupler 10 containing at least one open channel 10h may be packaged with a gel 15 present on and/or in a coupler body 10b and upon opening the package 20 and/or prior to use of the coupler 10, the package 20 has no or less than 10% of the initial volume of the gel 15 present on the base 20b of the package 20 (FIG. 22B).

Figure 2A:
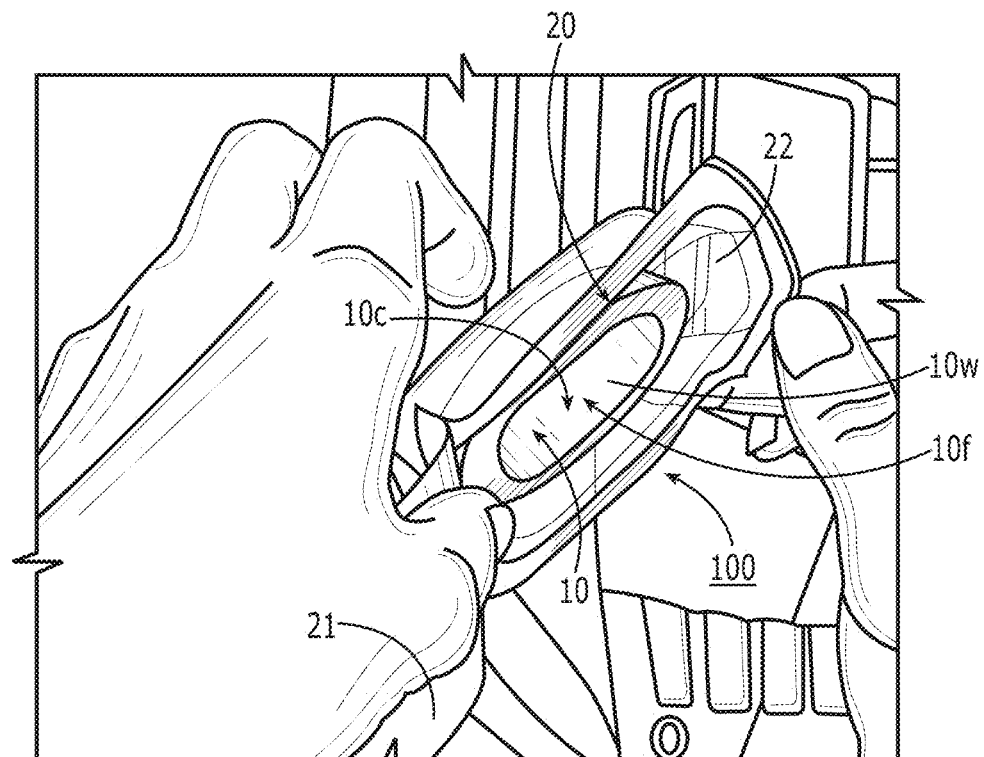
FIGS. 2A-2D are side perspective views of a sequence of actions that can be used to attach the coupler to the ultrasound probe according to embodiments of the present invention.
Figure 2B:
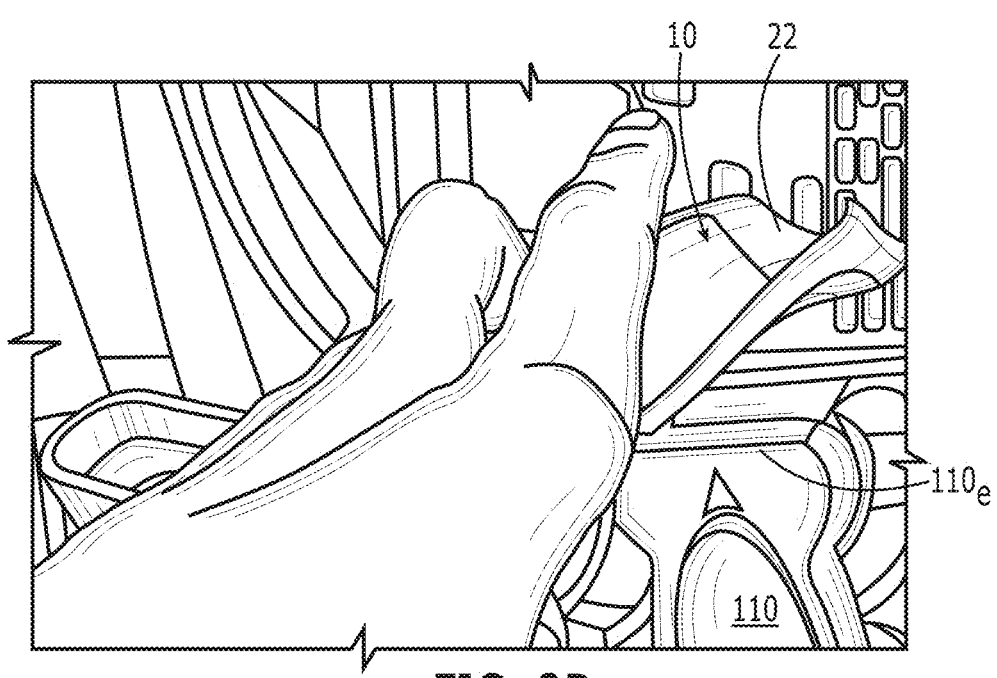
Figure 2C:
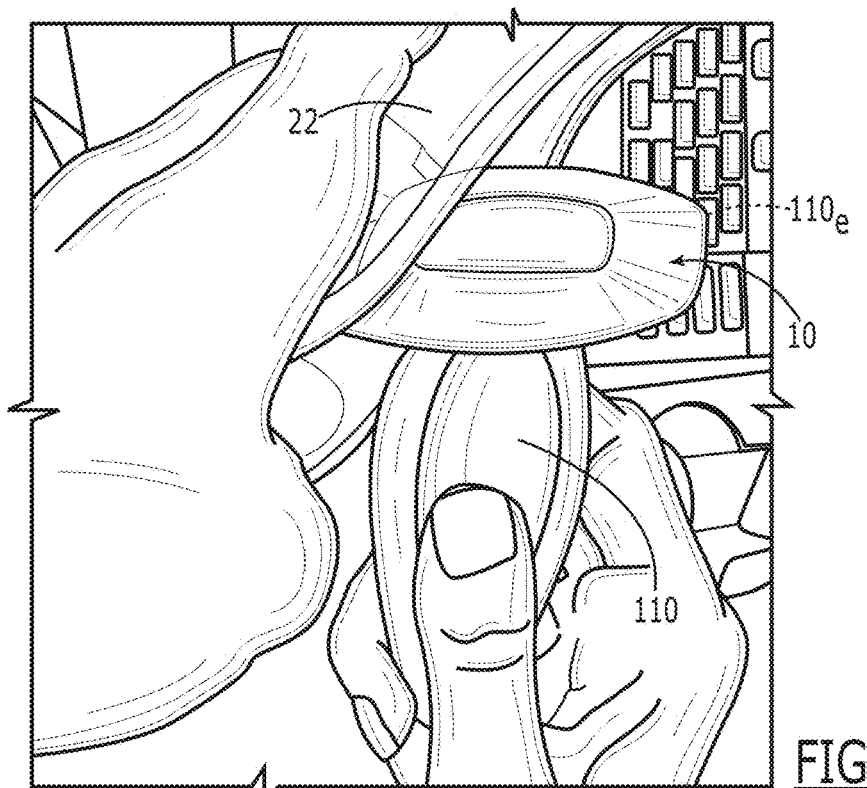
Figure 2D:
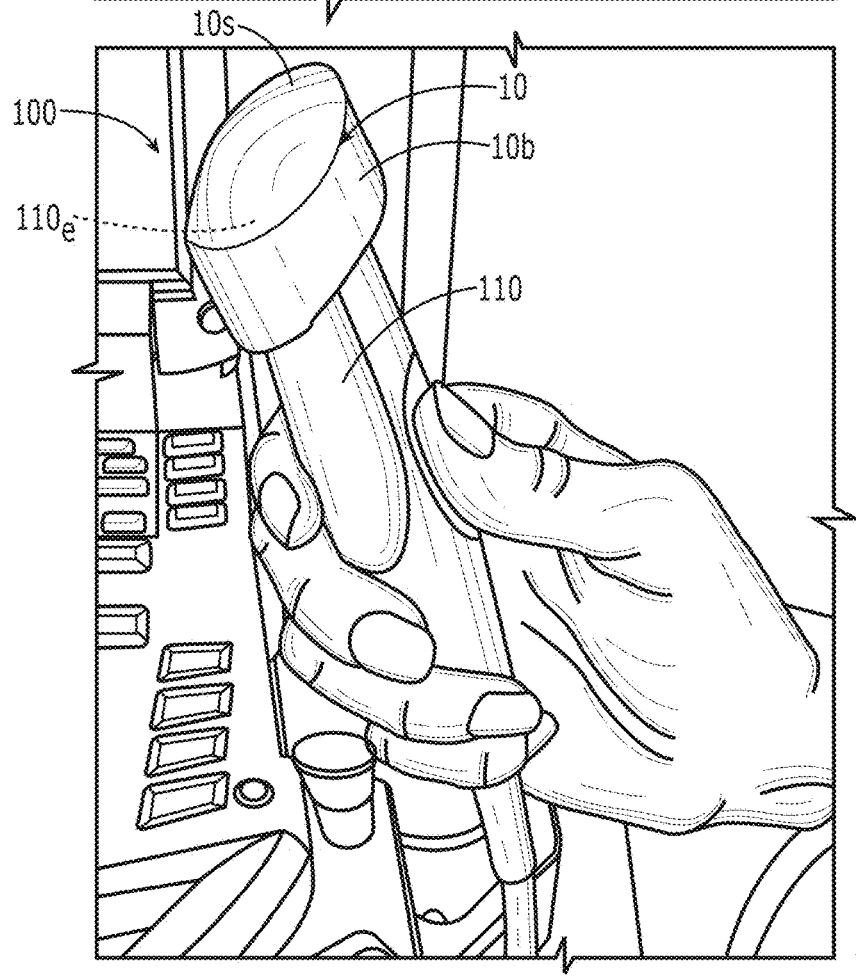
Figure 2E:
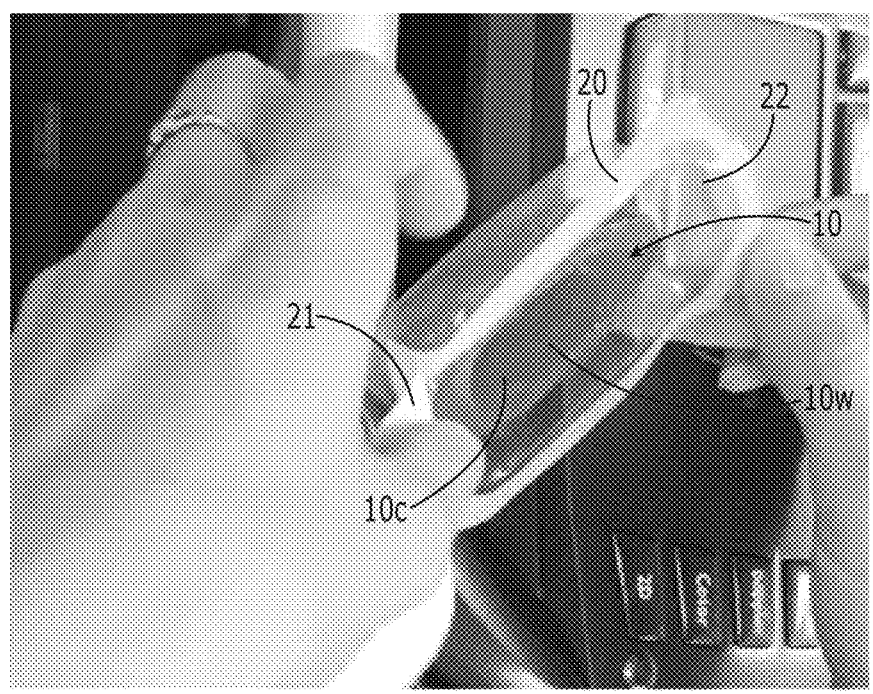
FIG. 2E is a digital photograph of a prototype corresponding to the device shown in FIG. 2A.

As shown in FIGS. 1, 2A and 2E, for example, the coupler 10 can be provided in a package 20, such as a sterile container, which can be easily opened to expose the coupler 10. Referring now to FIGS. 22A-22D, a package 20 may comprise at least one internal protruding member 20p that extends upwardly from a base 20b of the package 20. A coupler body 10b may be positioned inside a perimeter space defined by the at least one protruding member 20p in the package 20 (FIG. 22B). In some embodiments, the protruding member 20p may stabilize and/or hold the coupler body 10b in a desired position in the package 20, which may aid and/or allow for "one-hand" user attachment of the coupler 10 to a probe 110.

In some embodiments, the probe attachment member 50 may reside over at least one protruding member 20p in the package 20. For example, the probe attachment member 50 may be a sheath 50s having a holding member 50e, and the holding member 50e may extend down about the protruding member 20p in an expanded configuration with the sheath 50s draped over the protruding member 20p and an upper portion of the sheath 50s extending down over the protruding member 20p (FIG. 22B). The protruding member 20p may include a laterally outwardly extending ridge 20r, and the ridge 20r may keep the holding member 50e in the expanded configuration about the protruding member 20p until a force is exerted on the coupler body 10b that is sufficient to move the holding member 50e up past and/or over the ridge 20r. For example, when a target probe 110 is contacted to the coupler 10 while exerting a downward force F against the coupler body 10b, the holding member 50e may move up over the ridge 20r and over the protruding member 20p (FIG. 22C). This may allow for the sheath 50s and holding member 50*e* to move upwardly on its own without requiring manipulation by a user to reside about a target probe 110 (FIG. 22C) and the holding member 50*e* may contract to a non-expanded configuration (FIG. 22D). Alternatively, a user may release the sheath 50*s* and pull the sheath 50*s* up about a probe 110 and may tighten and/or clasp the holding member 50*e* about a portion of the probe 110.

Referring to FIG. 1, in some embodiments, the package 20 can include a peelably releasable cover 21, such as, for example, over a package pocket 22. The pocket 22 can hold the coupler 10 with a cavity 10*c* facing the cover 21. To assemble, as shown in FIG. 1, the package 20 can be held with the coupler cavity 10*c* facing up or as shown in FIG. 2B, with the coupler cavity 10*c* facing down as shown in FIG. 2B, to allow a user to merely insert the probe 110*e* into the cavity 10*c* (FIGS. 2B, 2C) and press the end of the probe 110*e* against the floor 10*f* (FIG. 4A) of the coupler cavity 10*c* to attach the coupler 10 to the probe 110 without requiring any attachment device or other user action (FIG. 2D). For example, unlike flexible thin stretchable/expandable sheaths which can be relatively cumbersome to attach to a probe 110, a press-fit and/or single-push action attachment is all that is required to attach the coupler 10 to the end of the probe 110*e* allowing for easier and faster assembly. This may facilitate compliance with use of the device, even during emergency situations, thereby promoting sterile uses of the ultrasound probe between patients without requiring the use of ultrasound gel on the skin of the patient.

FIGS. 2A-2C illustrate an exemplary sequence of actions that can be carried out to easily attach the coupler 10 to the probe 110 to thereby provide a sterile and suitable patient interface for sliding the ultrasound probe 110 and coupler 10, attached together, over the skin of the patient while the end of the probe 110*e* is held inside the cavity 10*c* of the coupler, snugly attached to the coupler 10. FIG. 2D shows the secure attachment in a ready-to-use state of the assembly of the coupler 10 and ultrasound probe 110.

Figure 3A:
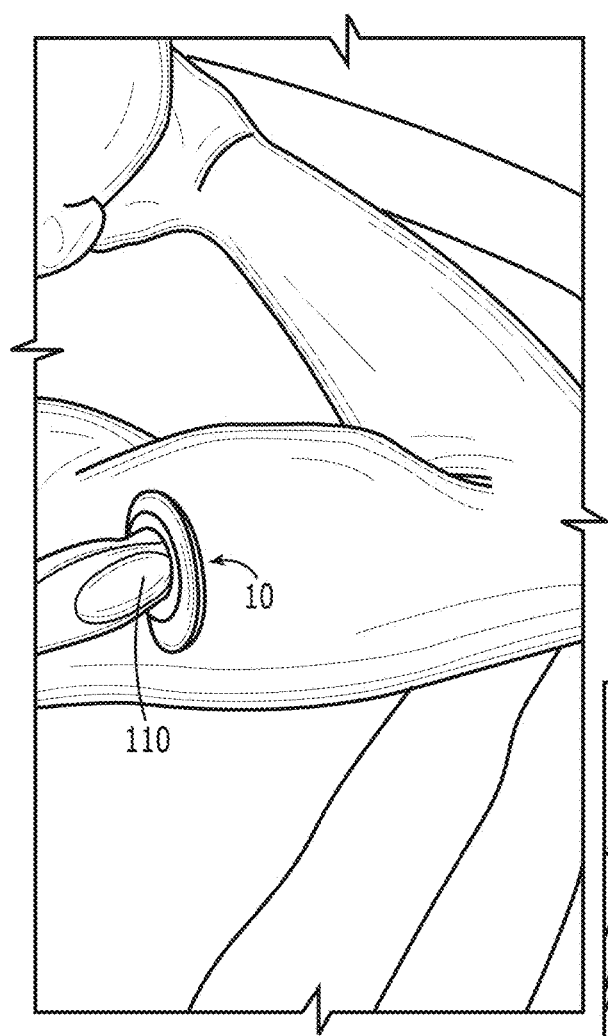
FIG. 3A is a side perspective view of the ultrasound coupler shown in FIG. 1 attached to the ultrasound probe according to embodiments of the present invention.
Figure 3B:
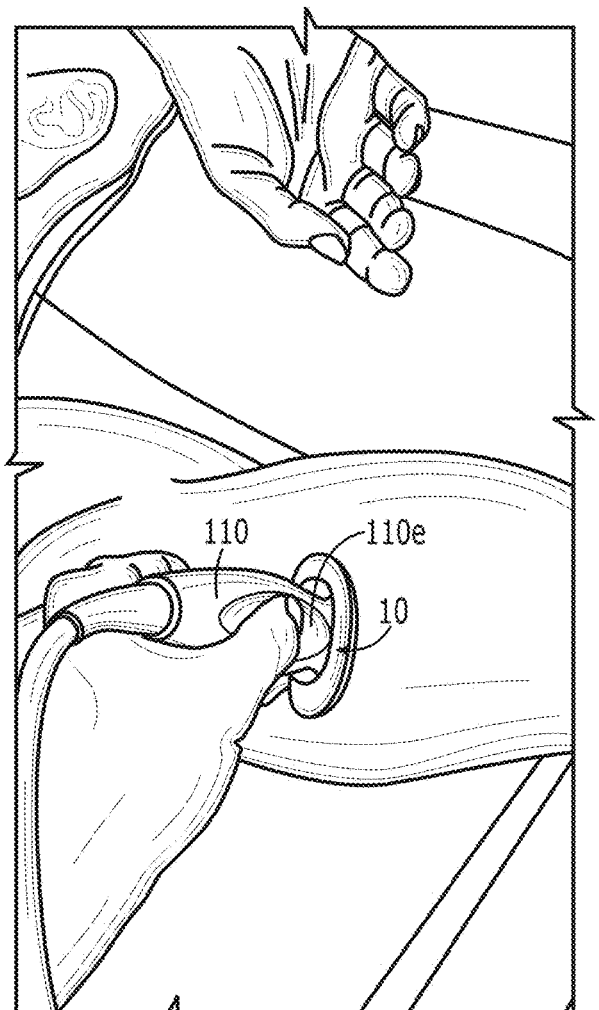
FIG. 3B is a top perspective view of the ultrasound coupler attached to the ultrasound probe, sliding across skin of a patient for an ultrasound evaluation according to embodiments of the present invention.

FIGS. 3A and 3B illustrate that the coupler 10 remains attached to the probe 110 during an ultrasound evaluation, sliding with the probe 110 as an integral unit or assembly, over the skin of the patient.

Figure 4A:
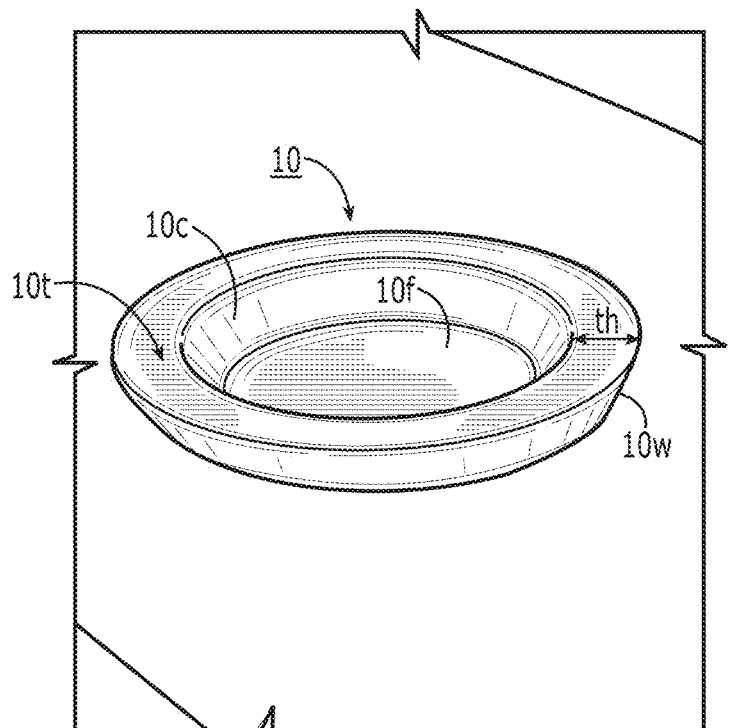
FIG. 4A is an enlarged, top perspective digital photograph of an exemplary coupler according to embodiments of the present invention.
Figure 4B:
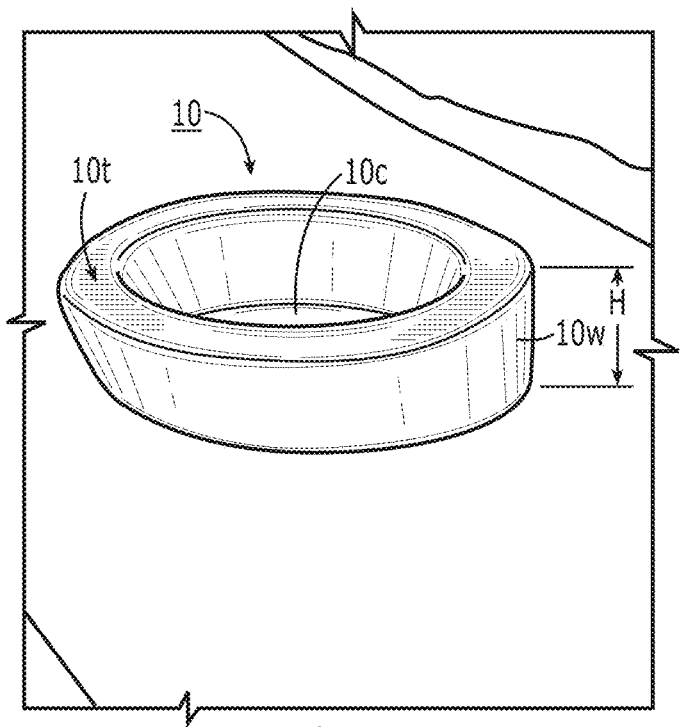
FIG. 4B is an enlarged, side perspective digital photograph of the exemplary coupler shown in FIG. 4A.

FIGS. 4A (and 4D) and 4B illustrate enlarged views of a prototype of an exemplary coupler 10. The coupler 10 can have a pre-formed cavity 10*c* of suitable depth so as to self-attach to an end of a target ultrasound probe 110*e*. The top of the coupler 10*t* can have a perimeter that extends about the open cavity 10*c* and can be sized and configured to expose a closed bottom floor 10*f* of the coupler that resides between the probe end 110*e* and the patient to provide a sterile interface/barrier. The sidewall 10*w* can taper out from the floor 10*f* or be substantially orthogonal to the floor 10*f* from the floor to the top 10*t*. FIG. 4D is a digital photograph of a prototype coupler 10 corresponding the coupler 10 shown in FIG. 4A.

Figure 4C:
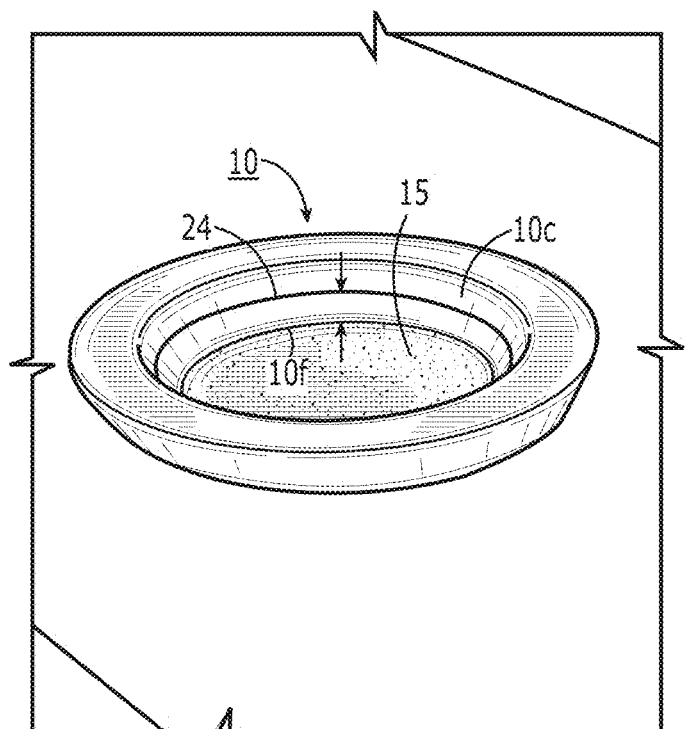
FIG. 4C is an enlarged, side perspective view of an exemplary coupler which includes a layer of ultrasonic fluid, e.g., gel held by the coupler according to embodiments of the present invention.
Figure 4D:
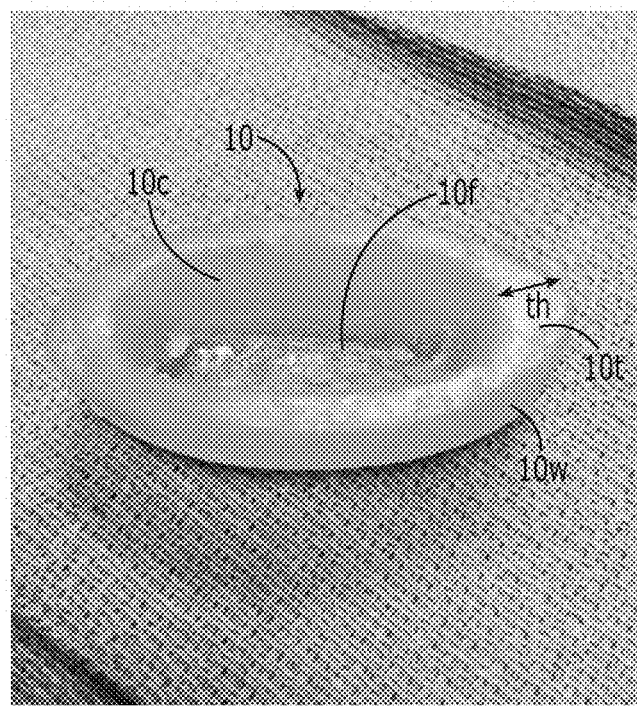
FIG. 4D is a digital photograph of a prototype of the device shown in FIG. 4A.
Figure 4E:
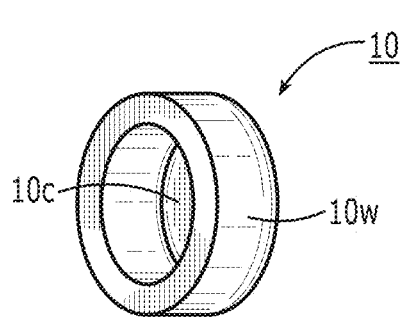
FIG. 4E is a top, side perspective view of an exemplary coupler according to embodiments of the present invention.
Figure 4F:
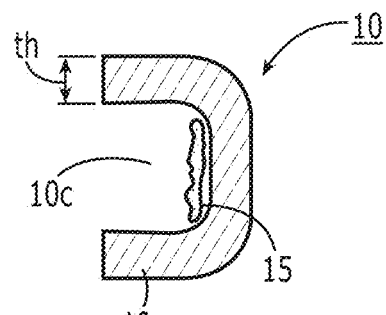
FIG. 4F is a sectional view of the coupler shown in FIG. 4E with optional gel in the cavity thereof according to embodiments of the present invention.

FIG. 4E is a top, side perspective view of an exemplary coupler 10 illustrating the sidewall 10*w* and cavity 10*c*. FIG. 4F is a section view of the coupler shown in FIG. 4E illustrating an optional gel 15 in the cavity 10*c* of the coupler 10 over the floor of the coupler 10*f* according to some embodiments.

The sidewall 10*w* can have a thickness (th) that is less than, the same or greater than a thickness of the floor 10*f*. In some embodiments, the sidewall 10*w* can have a thickness that is between two and twenty times the thickness of the floor. In some embodiments, the floor 10*f* can have a thickness that is between about 0.1 mm and about 12 mm, such as about 0.1 mm, about 0.2 mm, about 0.3 mm, about 0.4 mm, about 0.5 mm, about 0.6 mm, about 0.7 mm, about 0.8 mm, about 0.9 mm, about 1 mm, about 2 mm, about 3 mm, about 4 mm, about 5 mm, about 6 mm, about 7 mm, about 8 mm, about 9 mm, about 10 mm, about 11 mm, and about 12 mm. In some particular embodiments, the floor 10*f* can have a thickness between about 0.5 mm and about 1 mm.

The cavity 10*c* can be encased by the perimeter sidewall 10*w*. In other embodiments, the sidewall 10*w* is not required to be continuous about the cavity and the thickness from one or both a top to bottom or about the perimeter can vary. The coupler 10 can have a pre-formed shape with an open top 10*t* that has a perimeter shape that remains substantially, if not totally, the same after attachment to the end of the probe 110.

The sidewall 10*w* can have thickness dimension "th", on average, that is between about 0.1 mm and about 25 mm, more typically between about 1 mm and about 12 mm, such as about 1 mm, about 2 mm, about 3 mm, about 4 mm, about 5 mm, about 6 mm, about 7 mm, about 8 mm, about 9 mm, about 10 mm, about 11 mm, and about 12 mm. The sidewall 10*w* can define a cavity with a height H that is between about 0.1 mm and about 50 mm, more typically between about 10 mm and about 25 mm. The sidewall 10*w* can extend above the floor 10*f* a distance between about 5 mm and about 25 mm, in some embodiments.

The cavity 10*c* can have a size and shape that corresponds to a shape of a target end of an ultrasound probe 110. As shown, the cavity 10*c* can be oval and/or have a long dimension that is about 2× to about 5× longer than a short dimension thereof, but other sizes and shapes are contemplated. FIGS. 5, 6, 7A, 7B, 8A, 8B, 9A, 9B, 10A and 10B illustrate examples of couplers 10 and correspondingly shaped ends 110*e* of respective ultrasound probes 110.

FIGS. 4C and 4F illustrate that the coupler 10 may optionally be used with a gel and/or liquid 15 in the cavity to facilitate a probe-coupler interface for facilitating suitable ultrasound transmission. The gel and/or liquid 15 may be pre-loaded in the probe for ease of use or a clinician may insert the gel or liquid prior to assembly of the coupler 10 to the probe 110. The cavity 10*c* may include visual indicia 24 to allow a user to visually confirm a constant or consistent amount of gel or liquid is used. If needed, a liner or cover can be used to keep the gel or liquid in place or the container 20 can be shaped so as to hold the gel/liquid 15 in the cavity prior to use, if pre-applied to the coupler 10.

Figure 5:
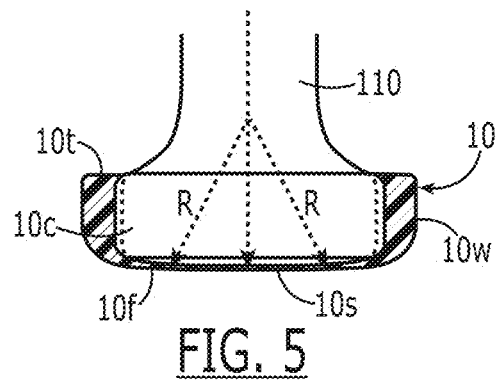
FIG. 5 is a schematic illustration of an ultrasound probe with a convex end attached to an exemplary coupler with an external convex shape according to embodiments of the present invention.

FIG. 5 illustrates that the floor 10*f* can have a shape that is convex so as to have a radius of curvature R that corresponds to the end of the probe 110*e*.

The coupler body can be entirely or have at least a bottom surface that is tacky to touch. The tackiness can be similar to that of a solid deodorant stick. To assess whether a material is tacky (sticky to the touch), a user can feel the coupler to see if it is sticky to the touch. This is in contrast to a slippery, wet liquid or gel, for example.

Figure 6:
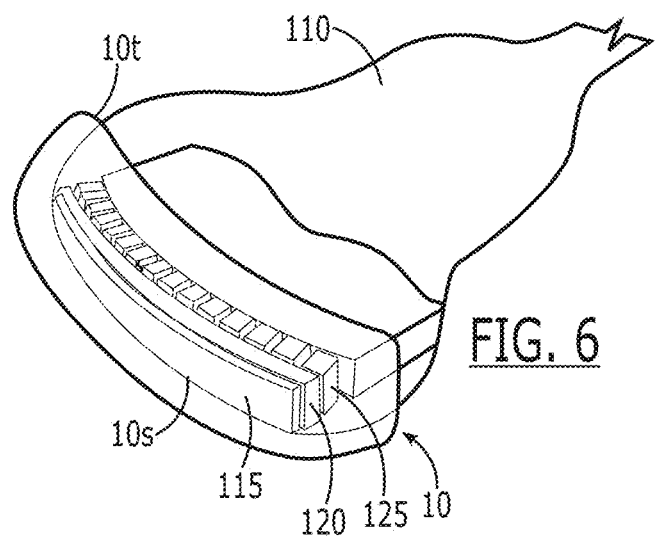
FIG. 6 is a schematic illustration of an exemplary ultrasound probe held inside an exemplary coupler according to embodiments of the present invention.
Figure 7A:
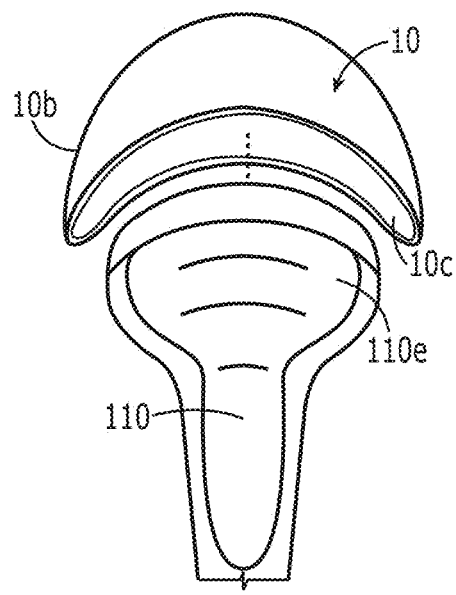
FIG. 7A is a schematic illustration of a pre-attached view of a coupler adjacent a target ultrasound probe according to embodiments of the present invention.
Figure 7B:
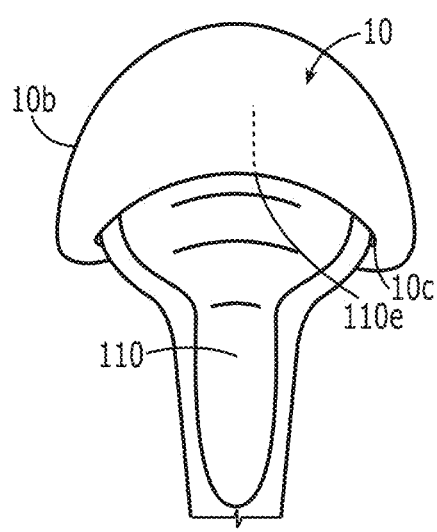
FIG. 7B is a schematic illustration of the assembled view of the coupler and probe shown in FIG. 7A.

FIG. 6 illustrates the coupler 10 can be elongate with a long dimension greater than a short dimension both in a pre-formed, pre-attached shape and a post-attached shape. The shape of the cavity 10*c* can correspond to the shape of the end of the probe 110*e*. The coupler 10 sidewall 10*w* can extend a short height H that can encase, reside above, an acoustic lens 115, acoustic matching layer 120, and/or transducer 125 in the end of the probe 110*e*. It is contemplated that different couplers can have different shapes to fit different ultrasound probes and those shown herein are by way of example and are not intended to be limiting.

FIGS. 7A, 7B, 8A, 8B, 9A, 9B, 10A and 10B show examples of a press-fit attachment that allows the coupler 10 to self-attach to the end of the probe 110e so as to be detachably, snugly coupled to the probe without requiring any further fixation.

In some embodiments, the end of the probe 110e can be compressed against at least an inner surface of the floor 10f to abut the outside surface of the end of the probe 110e and/or to form the probe/skin interface. The end of the ultrasound probe 110 can press-fit against the floor 10f and/or sidewall 10w so as either (i) self-attach to the end of the probe and/or (ii) to conform to a shape of the adjacent portion of the probe 110. Thus, for example, a user can press the end of the probe 110e against a surface of coupler, e.g., a floor or a cavity, to cause (i) the coupler to attach to the probe and substantially maintain its pre-formed exterior shape and/or (ii) bottom shape change in a wall, surface or floor thereof, by a user manually applying a relatively small, finger or hand applied force, while maintaining a three-dimensional shape.

The coupler 10 is typically single-use disposable and releasably attachable to the probe 110.

The coupler 10 can have a body that is formed of a unitary (single) monolithic material. In some embodiments, the coupler 10 can have a body that is formed of a plurality of different materials.

The coupler 10 can be configured to not require fixation devices as the coupler 10 can have a malleable body to be self-attaching to the probe 110. However, the coupler 10 may be configured to cooperate with securing or attachment devices to attach to the probe 110.

The coupler 10 can comprise a solid material composition corresponding to a solid deodorant stick with suitable (ultrasonic/acoustic) transmissive properties. In the prototype shown in FIGS. 4A, 4D and 4B, an OLD SPICE® PURE SPORT deodorant stick (Red Zone Collection) was used to make the coupler 10, which surprisingly had good ultrasound wave reception qualities as shown in FIG. 16B (by way of comparison to ultrasound gel in FIG. 16A).

The coupler 10 can have a monolithic unitary body with a defined, self-supporting, three-dimensional shape having an open upwardly facing cavity.

The coupler 10 can have at least the bottom surface with a lubricious material allowing the coupler 10 to easily slide over the skin with the probe end 110e held inside the cavity. The coupler 10 can have a self-lubricating outer surface that does not require ultrasound gel on the skin of the patient. The self-lubricating outer surface 10s can have a dry coat or a material that if tacky or wet, dries on contact with the skin without requiring any post-ultrasound clean-up and the patient/subject does not feel that the coupler 10 is cold to the touch in contrast to conventional use of ultrasound gel.

The probe 110 can be inserted into the coupler cavity 31 and pressed against the bottom of the cavity 10c causing the coupler body 10b to mold against and attach to the ultrasound probe. The coupler body has a sidewall 10w and/or floor 10f that can change its shape as it is compressed and closes against the ultrasound probe typically by inserting the ultrasound probe in the using one-press. To remove the coupler 30, a user can simply pull the coupler body away from the probe 20.

The coupler 10 can be visually and/or optically translucent or transparent. The coupler 10 can be visually opaque but ultrasonically transmissive so that the ultrasound waves are transmitted and received without undue loss of signal.

The coupler 10 can have a solid body 10b with a lubricious bottom surface so as to be able to slide over skin without undue friction (e.g., a low sliding friction value). The bottom surface can be "tacky" or somewhat "sticky" to touch, similar to a solid deodorant and/or antiperspirant stick.

The coupler 10 can be configured with a material that can easily slide over the skin of a patient while attached to the probe 110 without leaving wet residue, thus not requiring much, if any, post-use cleaning of the patient.

The coupler 10 can comprise a material that releases residue or small amounts of the material of the bottom (skin contact) surface 10s of the coupler body 10b, e.g., shed, release or apply micro-layers, as it is slides over skin of a patient, similar to the application of a deodorant stick. The temperature of the patient body may sufficiently heat the material to facilitate the release of the residue or small amounts of material in response to sliding over the skin. Thus, the coupler 10 while being configured to apply, release or shed material onto patient skin in response to sliding contact therewith, as it is slid over the patient skin, can be configured to retain between 95-99.999% of its bottom floor thickness over an imaging session.

The coupler 10 may have a defined color and/or scent. For pediatric uses, the scents can be fruity and/or candy related scents. For example, the coupler can have a purple color and a grape scent, a red color and an apple scent or an orange color and orange scent. The coupler may have a 3-D toy or animal theme or shape, e.g., an animal head or foot shape.

FIGS. 11A and 11B schematically illustrate the couple 10 with a press-fit attachment to the end of the ultrasound probe 110e provided by embodiments of the invention. FIG. 11A shows a pre-formed three-dimensional semi-rigid coupler body 10b ready for attachment. FIG. 11B schematically illustrates an exemplary compressive force vectors Fc that is applied orthogonal to the floor 10f. FIG. 11B also illustrates optional side-side compressive force vectors F that may optionally be used to attach the coupler 10.

Figure 12A:
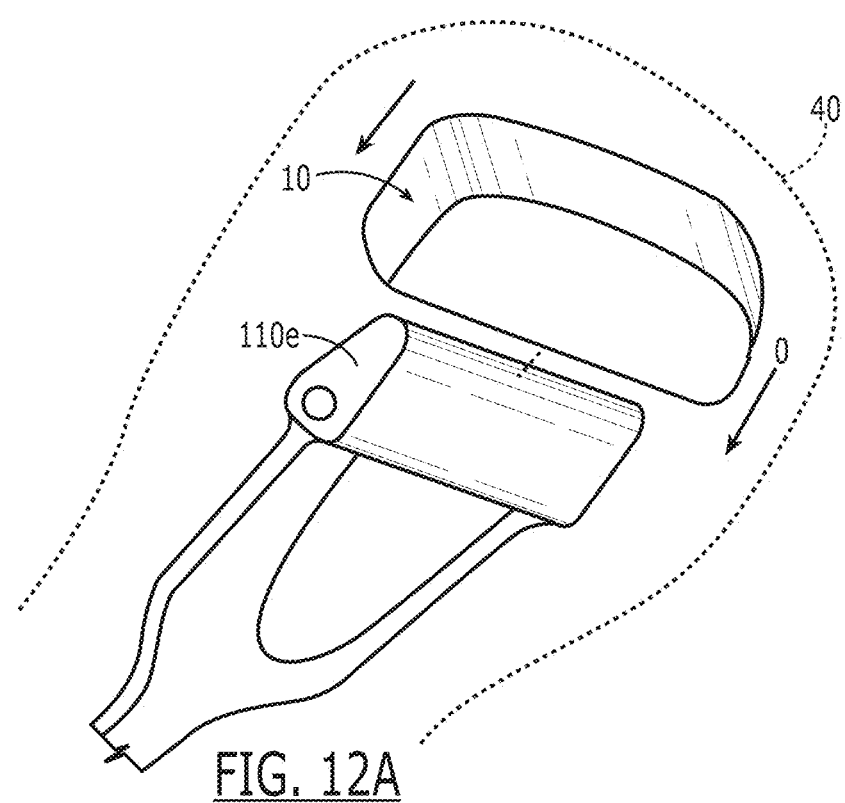
FIGS. 12A and 12B are side perspective views of an ultrasound probe with a coupler and external sheath according to embodiments of the present invention.
Figure 12B:
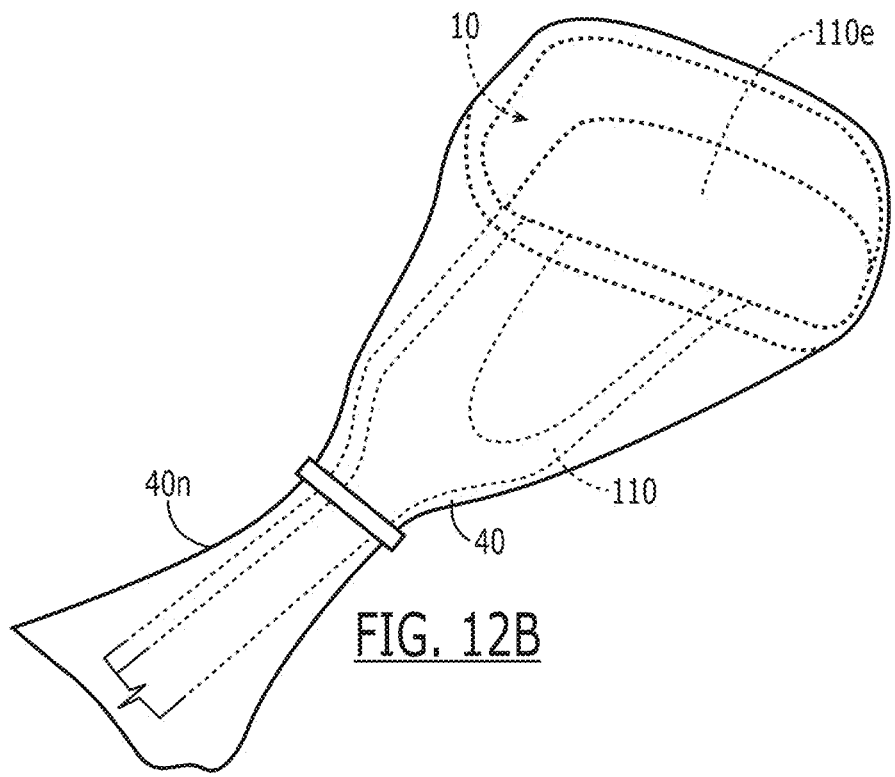

FIGS. 12A and 12B are side perspective views of an ultrasound probe 110e with a coupler 10 and an optional external sheath 40 according to embodiments of the present invention. The external sheath 40 can be flexible and bag-like (e.g., it can be rolled or folded and is not self-supporting) and can encase the distal end of the probe 110e as well as the coupler 10 attached thereto. The sheath 40 may provide a sterile interface between the patient and probe 110 and/or coupler 10. The sheath 40 can include a neck portion 40n that extends above the coupler and can be releasably attached to the probe 110.

Figure 13:
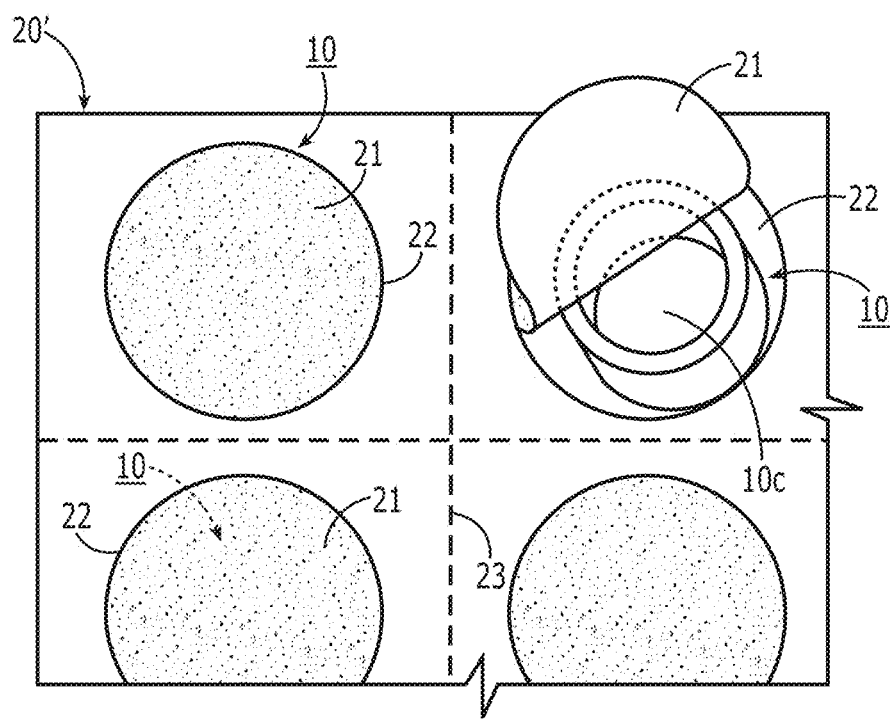
FIG. 13 is a schematic illustration of a multiple pack package according to embodiments of the present invention.

FIG. 13 illustrates a multiple pack package 20' which can provide a plurality of couplers 10 in a sterile condition and ready for use. The package 20' can include a plurality of cavities 22 that hold respective couplers 10 and the couplers 10 can reside under peel-way covers 21 with coupler cavities 10c facing outward, for ease of access. The package 20' can optionally include perforated or thinner wall regions 23 to allow a user to separate segments of the package 20.

Figure 14A:
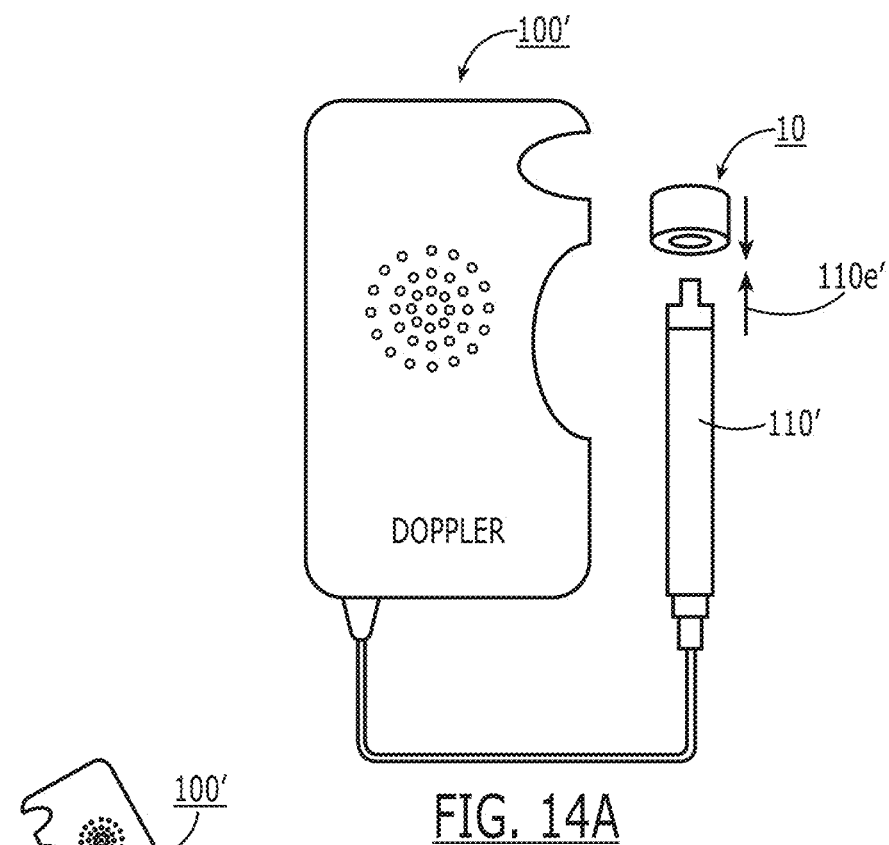
FIG. 14A is a schematic illustration of a portable Doppler ultrasound system according to embodiments of the present invention.
Figure 14B:
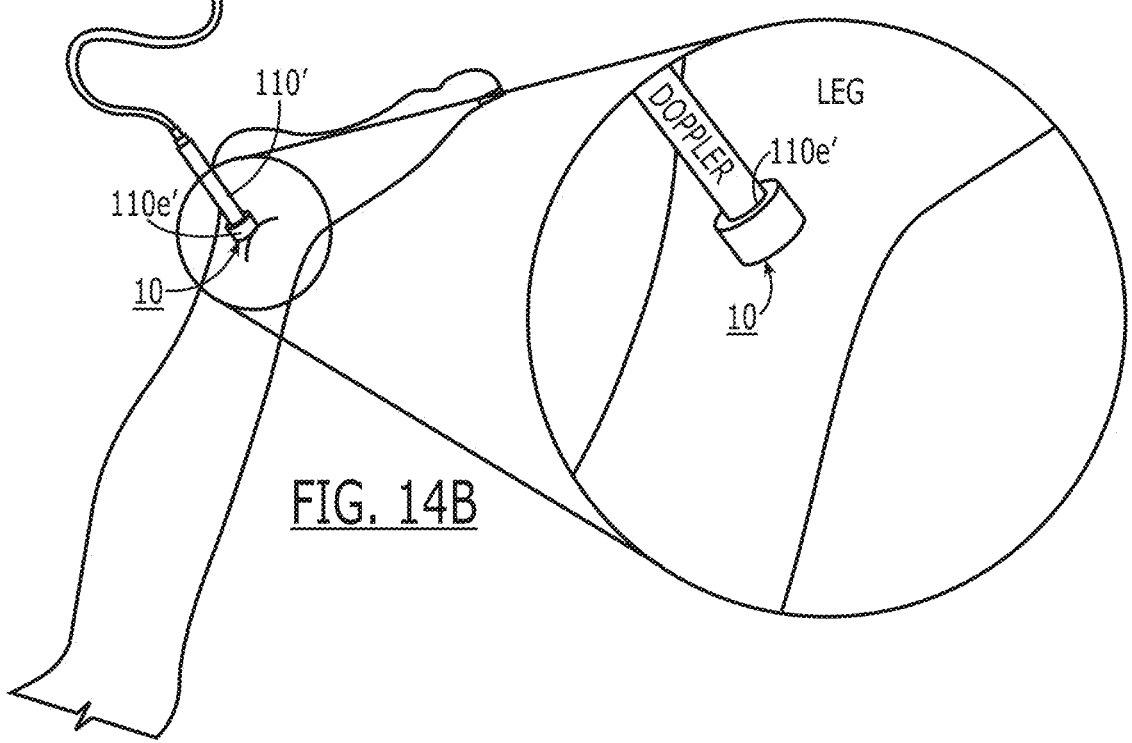
FIG. 14B is a schematic illustration of the Doppler system in use on a patient with a coupler according to embodiments of the present invention.

FIGS. 14A and 14B illustrate that the ultrasound system 100' can be a portable Doppler ultrasound system with an ultrasound probe 110' and a probe end 110e' configured to press-fit attach to the ultrasound coupler 10.

Figure 15:
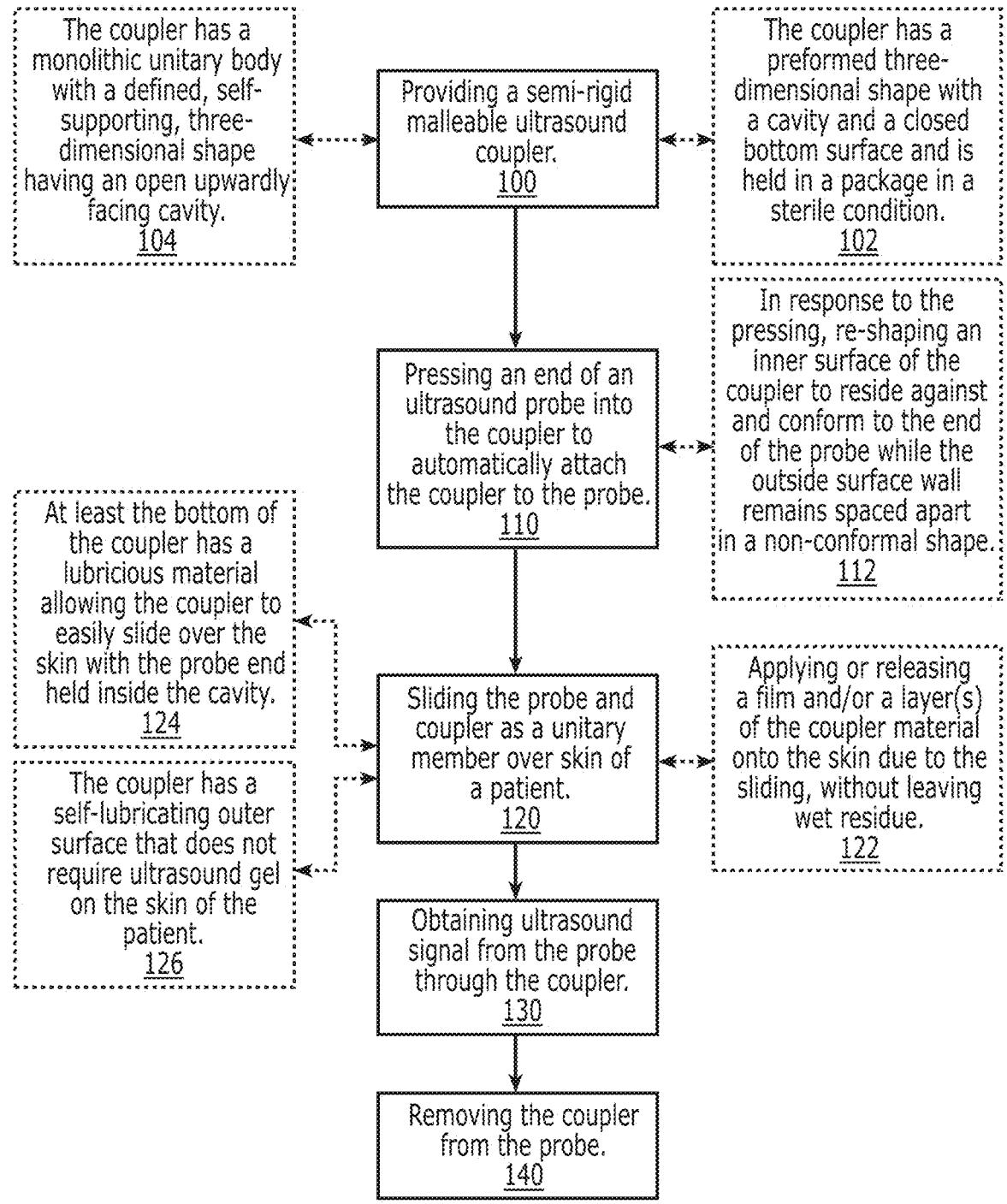
FIG. 15 is a flow chart of exemplary actions that can be used to attach a coupler to the ultrasound and carry out an ultrasound procedure according to embodiments of the present invention.

FIG. 15 illustrates exemplary actions that can be used to perform an ultrasound using a coupler 10. A semi-rigid, malleable ultrasound coupler is provided (block 100). An end of an ultrasound probe is pressed into the coupler to automatically attach the coupler to the probe (block 110). The probe and coupler are slid as a unitary member over skin of a patient (block 120). Ultrasound signal of the subject is obtained from the probe through the coupler (block 130). The coupler can be removed from the probe (block 140).

The coupler can have a preformed three dimensional shape with a cavity and a closed bottom surface and is held in a package in a sterile condition (block 102).

In response to the pressing, an inner surface of the coupler can be re-shaped to reside against and conform to the end of the probe while the outside surface wall remains spaced apart in a non-conformal shape (block 112).

A film and/or a layer(s) of the coupler material can be applied and/or released onto the skin due to the sliding, without leaving liquid wet residue to thereby avoid requiring post-clean up of gels like conventional ultrasound gel uses (block 122).

The coupler can have a monolithic unitary body with a defined, self-supporting, three-dimensional shape having an open upwardly facing cavity (block 104).

At least the bottom of the coupler can have a lubricious material allowing the coupler to easily slide over the skin with the probe end held inside the cavity (block 124).

The coupler can have a self-lubricating outer surface that does not require ultrasound gel on the skin of the patient (block 126).

Figure 16A:
FIG. 16A is a screen shot of a display with an ultrasound image obtained using conventional ultrasound gel on skin of a patient.
Figure 16B:
FIG. 16B is a screen shot of the display with an ultrasound image obtained using the semi-rigid coupler shown in FIGS. 4A, 4D.

FIG. 16A illustrates an ultrasound image obtained with an ultrasound probe and conventional ultrasound gel. FIG. 16B illustrates an ultrasound image obtained using the same ultrasound probe and the coupler shown in FIG. 4A. A coupler 10 of the present invention may comprise a polyhydric alcohol, a thickening agent, a surfactant, and/or water. In some embodiments, a polyhydric alcohol may be present in the coupler at a concentration in a range of about 1% to about 90% by weight of the coupler, a thickening agent may be present in the coupler at a concentration in a range of about 1% to about 15% by weight of the coupler, a surfactant may be present in the coupler at a concentration in a range of about 1% to about 30% by weight of the coupler, and/or water may be present in the coupler at a concentration in a range of about 1% to about 50% by weight of the coupler.

In some embodiments, a coupler 10 may comprise a polyhydric alcohol, a thickening agent, a surfactant, water, and/or ethylenediaminetetraacetic acid (EDTA) or a salt thereof, such as, for example, tetrasodium EDTA and/or disodium EDTA. In some embodiments, a coupler 10 may comprise two or more polyhydric alcohols, two or more thickening agents, and/or two or more surfactants. Some embodiments include that a coupler may comprise dipropylene glycol, propylene glycol, sodium stearate, polypropylene glycol ether of myristyl alcohol (PPG-3 myristyl ether), water, and tetrasodium EDTA. The concentration of various components in the coupler (e.g., the polyhydric alcohol, thickening agent, surfactant, water, etc.) may be chosen in order to provide one or more desired coupler properties, such as hardness, payout, and/or residue properties.

In some embodiments, a polyhydric alcohol may function as a solvent. A polyhydric alcohol may comprise 2 to 6 carbon atoms and 2 to 6 hydroxyl groups. Example polyhydric alcohols include, but are not limited to, ethylene glycol, propylene glycol, 1,3-propanediol, trimethylene glycol, butylene glycol, diethylene glycol, dipropylene glycol, glycerin, sorbitol, xylitol and combinations thereof. In some embodiments, a coupler may comprise at least two polyhydric alcohols, such as, for example, 2, 3, 4, 5, or more polyhydric alcohols. Some embodiments include a coupler 10 that comprises propylene glycol and/or dipropylene glycol.

A polyhydric alcohol may be present in a coupler 10 in any suitable amount. In some embodiments, the amount or concentration of a polyhydric alcohol in a coupler 10 may be selected and/or adjusted to provide the desired coupler properties. In some embodiments, a polyhydric alcohol may be present in a coupler 10 at a concentration in a range of about 1% to about 90% by weight of the coupler, such as, for example, about 5% to about 60%, about 5% to about 35%, about 15% to about 75%, about 20% to about 70%, about 40% to about 60%, or about 50% to about 90% by weight of the coupler. In some embodiments, a polyhydric alcohol may be present in a coupler 10 at a concentration of about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, or 90% by weight of the coupler.

In some embodiments, a thickening agent may function as a gelling agent. In some embodiments, a thickening agent may comprise a fatty acid salt, such as, but not limited to, alkali metal, alkaline earth metal, aluminum, ammonium, and/or amine salts of $C_{4-22}$ fatty acids. In some embodiments, a $C_{4-22}$ fatty acid may be a salt of myristic acid, palmitic acid, stearic acid, behenic acid, oleic acid, margaric acid, linoleic acid, and/or linolenic acid. Example thickening agents include, but are not limited to, gelatin, starch (e.g., tapioca starch), xanthan gum, maltodextrin, pectin, agar, collagen, sodium stearate, potassium stearate, magnesium stearate, aluminum monostearate, sodium oleate, sodium palmitate, sodium arachidate, sodium behenate, diethylamine stearate, triethylamine stearate, triethylemine oleate, polysaccharides, guar gum, carrageenan, xanthan, gum tragacanth, gum Arabic, gum karaya, locust bean gum, coconut oil, beef tallow, lanolin, fish oil, beeswax, palm oil, peanut oil, olive oil, cottonseed oil, soybean oil, corn oil, rapeseed oil, and/or rosin acids. In some embodiments, the thickening agent comprises sodium stearate.

A thickening agent may be present in a coupler 10 in any suitable amount. In some embodiments, the amount or concentration of a thickening agent in a coupler 10 may be selected and/or adjusted to provide the desired coupler properties. In some embodiments, the concentration of a thickening agent in the coupler 10 may provide the desired hardness and/or firmness for the coupler 10. In some embodiments, a thickening agent may be present in a coupler 10 at a concentration in a range of about 1% to about 15% by weight of the coupler 10, such as, but not limited to, about 2% to about 10%, about 1% to about 5%, or about 5% to about 15% by weight of the coupler 10. In some embodiments, a thickening agent may be present in a coupler 10 at a concentration of about 1%, 2%, 3%, 4%, 5%, 6%, 7%, 8%, 9%, 10%, 11%, 12%, 13%, 14%, or 15% by weight of the coupler 10.

In some embodiments, a surfactant may function as a clarifying agent, solubilizier, and/or an emulsifier. In some embodiments, a surfactant may comprise a hydrophobic portion and a hydrophilic portion and/or may reduce the surface tension of the composition in which it is present and/or dissolved in. A surfactant may be nonionic, anionic, cationic, amphoteric, or zwitterionic. Example surfactants include, but are not limited to, polyethylene glycol 20, sorbitan monolaurate (Polysorbate 20), polyethylene glycol 20 stearyl ether (Brij 78, Steareth 20), polyethylene glycol ether of lauryl alcohol (Laureth 23), polysorbate 80 (Tween 80), polytrimethyene ether glycol laurate, pentadoxynol-200, tetra(hydroxypropyl)diamine, 2-amino-2-methylpropanol, 2-amino-2-hydroxymethyl-1,3-propanediol, poly($C_{2-4}$ alkylene) glycol ethers of $C_{2-22}$ fatty alcohols, propoxylated fatty alcohols, polypropylene glycol ether of $C_{12}$-$C_{22}$ fatty alcohols (e.g., polypropylene glycol ether of myristyl alcohol (PPG-3 myristyl ether)), laureth-10, laureth-20, laureth-30, laureth-40, polyethylene glycol ether of $C_{12}$-$C_{22}$ fatty alcohols (e.g., polyethylene glycol (PEG)-10 myristyl ether), steareth-10, steareth-20, steareth-40, steareth-100, PEG-50 stearyl ether, steareth-100, beheneth-20, polyoxyethylene 3-pentadecyl phenyl ether, and combinations thereof. In some embodiments, the surfactant is a poly($C_{2-4}$ alkylene) glycol ether of a $C_{2-22}$ fatty alcohol. In some embodiments, the surfactant is a propoxylated fatty alcohol. In some embodiments, the surfactant is a polypropylene glycol ether of a $C_{12}$-$C_{22}$ fatty alcohol and/or a polyethylene glycol ether of a $C_{12}$-$C_{22}$ fatty alcohol. In some embodiments, the fatty alcohol may be lauryl alcohol, myristyl alcohol, palm alcohol, stearyl alcohol and/or behenyl alcohol. In some embodiments, the surfactant may be PPG-3 myristyl ether.

A surfactant may be present in a coupler 10 in any suitable amount. In some embodiments, the amount or concentration of a surfactant in a coupler may be selected and/or adjusted to provide the desired coupler properties. In some embodiments, a surfactant may be present in a coupler at a concentration in a range of about 0.1% to about 30% by weight of the coupler, such as, but not limited to, about 1% to about 10%, about 0.1% to about 5%, or about 5% to about 20% by weight of the coupler. In some embodiments, a surfactant may be present in a coupler at a concentration of about 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, or 30% by weight of the coupler.

A coupler 10 may comprise water. In some embodiments, water may function as a solvent. Water may be present in a coupler in any suitable amount. In some embodiments, the amount or concentration of water in a coupler may be selected and/or adjusted to provide the desired coupler properties. In some embodiments, the balance or remainder of the composition weight may be water (i.e., water may make up the remaining weight percent to total 100%). In some embodiments, water may be present in a coupler at a concentration in a range of about 1% to about 50% by weight of the coupler, such as, but not limited to, about 1% to about 10%, about 1% to about 5%, about 5% to about 20%, about 10% to about 25%, about 1% to about 30%, about 25% to about 50%, about 20% to about 40%, or about 15% to about 20% by weight of the coupler. In some embodiments, water may be present in a coupler at a concentration of about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, or 50% by weight of the coupler.

A coupler 10 may comprise EDTA or a salt thereof, such as for example, tetrasodium EDTA and/or disodium EDTA. In some embodiments, EDTA or a salt thereof may function as a preservative, chelating agent, and/or neutralizing agent. EDTA or a salt thereof may be present in a coupler in any suitable amount. In some embodiments, the amount or concentration of EDTA or a salt thereof in a coupler may be selected and/or adjusted to provide the desired coupler properties. In some embodiments, EDTA or a salt thereof may be present in a coupler at a concentration of less than about 10% by weight of the coupler. In some embodiments, EDTA or a salt thereof may be present in a coupler at a concentration of about 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, or 10% by weight of the coupler.

A coupler 10 may comprise one or more additional components including, but not limited to, antimicrobial agents (e.g., triclosan, silver chloride, botanical extracts, etc.), therapeutic agents, preservatives, disinfectant agents, moisturizing agents, spreadability enhancing agents, glide agents, soothing agents, chelating agents (e.g., disodium EDTA, tetrasodium EDTA, etc.), neutralizing agents (e.g., aminomethyl propanol, poloxamine 1307, sodium hydroxide, tetrasodium EDTA, etc.), antioxidants (e.g., butylated hydroxytoluene, etc.), colorants, and/or fragrances. The one or more additional components may be selected to provide and/or improve the efficacy, stability, cosmetics, and/or aesthetics of a coupler, such as, for example the skin feel, glide properties, hardness, and/or payout. The one or more additional components may each be present in a coupler at a concentration of less than about 10% by weight of the coupler. In some embodiments, an additional component may be present in a coupler at a concentration of about 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, or 10% by weight of the coupler.

In some embodiments, a preservative may be present in a coupler 10 of the present invention. Example preservatives include, but are not limited to, benzyl alcohol, methyl paraben, propyl paraben, DMDM hydantoin, methylchloroisothiaoline, methylisothiazolinone, imidazolidinyl urea phenoxyethanol, sodium benzoate, benzoic acid, EDTA, and/or salts thereof. A preservative be present in a coupler at a concentration of less than about 10% by weight of the coupler. In some embodiments, a preservative may be present in a coupler at a concentration of about 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, or 10% by weight of the coupler.

In some embodiments, an alcohol may be present in a coupler 10 of the present invention. Example alcohols include, but are not limited to, denatured alcohol (e.g., specifically denatured alcohol), ethyl alcohol, isopropyl alcohol, and combinations thereof. An alcohol may be present in a coupler at a concentration of less than about 40% by weight of the coupler. In some embodiments, an alcohol may be present in a coupler at a concentration of about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, or 40% by weight of the coupler.

Further examples of components including materials and/or chemicals and/or their concentration that may be used in couplers 10 of the present invention and/or methods for combining one or more components to form a solid include, but are not limited to, those described in U.S. Pat. Nos. 2,857,315; 4,617,185; and 5,650,140; U.S. Patent Application Publication No. 2014/0271517; and International Publication No. WO 2009/046008, the contents of each of which are incorporated herein by reference for the portions relevant to this paragraph. The components and/or methods as described and/or incorporated herein may be used to form a coupler 10 that is ultrasonically transmissive or suitable for ultrasound rather than for use as a deodorant or antiperspirant. Thus, while these documents are referenced, they are intended to be by way of example only and different chemicals or features in one may be combined in any way with that from another or omit chemicals or materials not useful for or that may be undesired for the purposes of the devices of the present application.

Ultrasound couplers 10 of the present invention may have a satisfactory skin feel, satisfactory application aesthetics, satisfactory glide properties, satisfactory payout and/or no or minimal residue when contacted with the skin of a subject during an ultrasound imaging session. In some embodiments, the coupler 10 may have a satisfactory payout during use with normally exerted user pressure. In some embodiments, a coupler 10 may have excellent esthetics (e.g., smoothness, a comfortable dry feel, etc.) and no or minimal visually perceptible residue when contacted and/or applied to the skin of subject. One or more properties of the coupler 10 may be evaluated by the user of the coupler and/or by the subject contacted with the coupler 10.

The term "payout" as used herein, refers to the amount of material (e.g., the residue) that may be deposited on a subject's skin and/or a test apparatus from the coupler during use (e.g., contact with the subject's body and/or test apparatus). In some embodiments, the coupler may have a payout in an amount of about 0.1 mg/cm$^2$ to about 10 mg/cm$^2$, such as, for example, about 1 mg/cm$^2$ to about 6 mg/cm$^2$ or about 2 mg/cm$^2$ to about 4 mg/cm$^2$. In some embodiments, the coupler may have a payout in an amount of about 0.1, 0.2, 0.3, 0.4, 0.5, 0.6, 0.7, 0.8, 0.9, 1, 2, 3, 4, 5, 6, 7, 8, 9, or 10 mg/cm$^2$. Payout and/or other residue measurements (e.g., glide, flakeoff, Tan Delta, and Residue Grade values) may be as described in, for example, U.S. Patent Application Publication No. 2011/0076309 and International Publication Nos. WO 2001/087252 and WO 2009/045557 and/or measured using known methods, such as, but not limited to, those described in U.S. Patent Application Publication No. 2011/0076309 and International Publication Nos. WO 2001/087252 and WO 2009/045557, the contents of each of which are incorporated herein by reference for the portions relevant to this paragraph.

In some embodiments, a coupler 10 may have a hardness of about 150 gram-force to about 2,000 gram-force before residue is dispensed from the coupler, such as, for example, about 200 gram-force to about 400 gram-force, about 300 gram-force to about 600 gram-force, about 600 gram-force to about 800 gram-force, or about 800 gram-force to about 2,000 gram-force before residue is dispensed from the coupler. In some embodiments, a coupler 10 may have a hardness of about 150, 200, 250, 300, 350, 400, 450, 500, 550, 600, 650, 700, 750, 800, 850, 900, 950, 1000, 1100, 1200, 1300, 1400, 1500, 1600, 1700, 1800, 1900, or 2000 gram-force before residue is dispensed from the coupler. Hardness (e.g., penetration force (gram-force), static yield stress (Pa) values, and/or high shear stress viscosity) may be as described in, for example, U.S. Patent Application Publication Nos. 2014/0271516 and 2013/0108570 and International Publication No. WO 2001/087252 and/or measured using known methods, such as, but not limited to, those described in U.S. Patent Application Publication Nos. 2014/0271516 and 2013/0108570 and International Publication No. WO 2001/087252, the contents of each of which are incorporated herein by reference for the portions relevant to this paragraph.

In some embodiments, one or more different portions of a coupler 10 (e.g., the coupler outer surface 10s and coupler sidewall 10w) may have different hardness values. For example, the floor 10f of the coupler 10 can have a hardness that is less than that of the sidewall 10w. The reverse may also be true, the sidewall 10s can have a hardness that is greater than that of the floor 10f.

In some embodiments, the coupler 10 may comprise a single layer or two or more (e.g., 2, 3, 4, 5, 6, 7, 8, 9, 10, etc.) stacked layers of the same or different materials and/or the same or different chemical compositions. The two or more layers may be combined and/or attached to form the shaped body of coupler 10. In some embodiments, at least a portion of a probe attachment member 50 may be between two layers, which may secure and/or attach the probe attachment member 50 to the coupler body 10b. Thus, the probe attachment member 50 can extend from a side of the coupler body 10b. For example, as shown in FIG. 24A end portions 50ae, 50be of probe attachment members 50a, 50b are between a first layer of the coupler body 10b1 and a second layer of the coupler body 10b2. Alternatively, a middle portion 50m of a probe attachment member 50 can be between a first layer of the coupler body 10b1 and a second layer of the coupler body 10b2 (FIG. 24B).

In some embodiments, a coupler 10 may have a different composition in two or more different portions (e.g., two or more different layers) of the coupler 10. In some embodiments, the concentration of one or more ingredients may be different in two or more different portions and/or layers of a coupler 10 and/or a different ingredient may be present in at least one of the two or more different portions and/or layers of a coupler 10.

In some embodiments, the coupler 10 may comprise a first portion (e.g., first layer) and a second portion (e.g., second layer) and the first and second portions may have different compositions. In some embodiments, the composition of the first portion may more easily lubricate the skin of a patient and/or may be more lubricating compared to the composition of the second portion. Thus, the composition of the first portion may provide improved and/or increased lubrication to the skin of the patient and/or less force and/or friction on the skin of the patient compared to the composition of the second portion. In some embodiments, the portion and/or layer of the coupler 10 that includes the exterior surface of the floor 10f that may contact the skin of a patient may have a different composition that is more lubricating to the skin of a patient and/or more easy to lubricate the skin of a patient than another portion of the coupler 10.

In some embodiments, the coupler 10 may comprise at least two portions (e.g., layers) and one portion has a different concentration for at least one ingredient than another portion. For example, the concentration of an ingredient (e.g., a polyhydric alcohol, thickening agent, surfactant, and/or water) present in the exterior surface of the floor 10f that may contact the skin of a patient may be different than the concentration of the same ingredient in the interior surface of the floor 10f. In some embodiments, the concentration of an ingredient present in the floor 10f and/or coupler sidewall 10w may be different than the concentration of the same ingredient in the interior of cavity 10c. In some embodiments, the concentration of an ingredient present in the coupler outer surface 10s may be different than the concentration of the same ingredient in the coupler sidewall 10w. In some embodiments, a concentration gradient for at least one ingredient may be present in the coupler 10. For example, the coupler 10 may comprise water in a concentration gradient that increases in concentration as the coupler 10 extends distally from an ultrasound probe 110 or vice versa. Thus, the exterior surface of the floor 10f that may contact the skin of a patient may have a higher concentration of water than a portion of the coupler 10 that is closer to the ultrasound probe 110 (e.g., the portion of the floor 10f that is closer to and/or in contact with the ultrasound probe 110).

In some embodiments, the coupler 10 may comprise at least two portions (e.g., layers) and one portion may have a different ingredient than another portion. For example, one portion may include a surfactant and another portion may include a different surfactant. In some embodiments, the coupler 10 may comprise at least two portions (e.g., layers) and one portion may include an ingredient that is not present in another portion. For example, one portion may include a surfactant and another portion may not include a surfactant.

While the foregoing written description of the invention enables one of ordinary skill to make and use what is considered presently to be the best mode thereof, those of ordinary skill will understand and appreciate the existence of variations, combinations, and equivalents of the specific embodiment, method, and examples herein. The invention should therefore not be limited by the above described embodiment, method, and examples, but by all embodiments and methods within the scope and spirit of the invention as claimed.

That which is claimed:

1. An ultrasound coupler, comprising:
   an ultrasound coupler body having a self-supporting, three-dimensional shape; and
   two or more spaced-apart probe attachment members flexibly coupled to the coupler body, each probe attachment member having at least one segment capable of bending upwardly above the coupler body to engage a probe,
   wherein the ultrasound coupler body comprises a first material and the probe attachment members comprise a second material, and the first material and the second material are different, and
   wherein the ultrasound coupler body is a unitary member, and
   wherein each probe attachment member comprises an adhesive on an inner surface of the at least one segment such that the adhesive can releasably attach the probe attachment member to an outer surface of the probe.

2. The coupler of claim 1, wherein the two or more spaced-apart probe attachment members are each attached to a perimeter portion of the coupler body and extend only from first and second spaced apart ends of the coupler body.

3. The coupler of claim 1, wherein the two or more spaced-apart probe attachment members are sized and configured to be able to conform to at least two different sized target probes.

4. The coupler of claim 1, wherein the two or more spaced-apart probe attachment members comprise a first probe attachment member and a second probe attachment member that are laterally spaced apart about a perimeter of the coupler body.

5. The coupler of claim 1, wherein the length of each of the two or more probe attachment members is about 0.5 to about 8 inches.

6. The coupler of claim 1, wherein the coupler body comprises at least one open fluid channel that extends through the coupler body to define a fluid path, and wherein, responsive to a force exerted at a top surface of the coupler body, gel held in the coupler body moves through the at least one open fluid channel and out at a bottom surface of the coupler body.

7. The coupler of claim 6, wherein the gel is in a medial probe receiving cavity of the coupler body.

8. The coupler of claim 1, wherein the coupler body is malleable.

9. The coupler of claim 1, wherein the coupler body includes a sidewall and a floor, and the floor has a thickness that is less than a thickness of the sidewall.

10. The coupler of claim 1, wherein the coupler body comprises a lubricious material that facilitates sliding of the coupler and the probe as a unitary assembly over the skin of a subject.

11. The coupler of claim 1, wherein the coupler body is a monolithic unitary member.

12. The coupler of claim 1, in combination with an ultrasound probe, wherein the ultrasound probe has an end that is held in contact with the coupler body.

13. The coupler of claim 1, wherein the coupler body has a payout in an amount of about 0.1 mg/cm2 to about 10 mg/cm2.

14. A method of evaluating a subject, comprising:
   manually pressing a coupler of claim 1 against an outer end portion of an ultrasound probe with the coupler providing a skin to ultrasound probe interface;
   sliding the probe and the coupler together as a unitary member over skin of the subject to obtain ultrasound images; and
   detaching the coupler from the probe after an ultrasound imaging session.

15. The method of claim 14, further comprising applying or releasing material of the bottom surface of the coupler body onto the skin of the subject in response to the sliding step.

16. The method of claim 14, wherein in response to the sliding step, the coupler releases or sheds material that self-dries on the skin of the subject during the imaging session.

17. The coupler of claim 1, wherein the two or more spaced-apart probe attachment members are configured to flex and bend around a bottom portion of an ultrasound probe when the ultrasound probe is positioned in contact with the two or more spaced-apart probe attachment members.

18. The coupler of claim 1, wherein the adhesive is configured to releasably directly or indirectly attach to the outer surface of the probe.

19. The coupler of claim 1, wherein the adhesive is in the form of a sheet, film or glue.

20. The coupler of claim 1, wherein the two or more spaced-apart probe attachment members further comprise a polymer including the adhesive.

21. The coupler of claim 1, wherein the two or more spaced-apart probe attachment members further comprise an adhesive tape.

22. The coupler of claim 1, further comprising a releasable liner that is on a surface of the adhesive.

23. The coupler of claim 22, wherein the releasable liner is removable to allow the adhesive to be placed in contact with the probe.

24. The coupler of claim 1, wherein the at least one segment of each probe attachment member is configured to conformally adhere to at least a portion of the surface of the probe.

25. The coupler of claim 1, wherein the coupler body includes a cavity configured to receive an end of the probe.

26. The coupler of claim 1, wherein the coupler body has a different thickness than the probe attachment members.

* * * * *